United States Patent [19]
Danilewicz et al.

[11] Patent Number: 4,975,444
[45] Date of Patent: Dec. 4, 1990

[54] CYCLOALKYL-SUBSTITUTED GLUTARAMIDE ANTIHYPERTENSIVE AGENTS

[75] Inventors: John C. Danilewicz; Keith James; Ryszard J. Kobylecki, all of New York, N.Y.

[73] Assignee: Pfizer Inc., New York, N.Y.

[21] Appl. No.: 398,675

[22] Filed: Aug. 25, 1989

[30] Foreign Application Priority Data

Sep. 5, 1988 [GB] United Kingdom ............. 8820844.2

[51] Int. Cl.$^5$ .................. A61K 31/195; A61K 31/24; C07C 229/10
[52] U.S. Cl. ..................... 514/354; 514/403; 514/404; 514/419; 514/423; 514/428; 514/467; 514/471; 514/481; 514/484; 514/488; 514/510; 514/530; 514/562; 514/563; 546/323; 548/342; 548/372; 548/495; 548/539; 548/567; 549/229; 549/487; 560/10; 560/12; 560/13; 560/27; 560/28; 560/38; 560/39; 560/41; 560/115; 560/118; 562/427; 562/430; 562/443; 562/444; 562/450; 562/500
[58] Field of Search ............... 548/372, 495, 342, 539, 548/567; 560/13, 41, 10, 12, 27, 28, 37, 39, 115, 118; 562/430, 450, 437, 443, 444, 449, 500; 546/323; 549/229, 487; 514/354, 403, 404, 419, 423, 428, 467, 471, 481, 484, 488, 510, 530, 562, 563

[56] References Cited

FOREIGN PATENT DOCUMENTS 103077 3/1984 European Pat. Off. .
225292 6/1987 European Pat. Off. .
274234 7/1988 European Pat. Off. .
00066 1/1986 PCT Int'l Appl. .

Primary Examiner—Richard L. Raymond
Attorney, Agent, or Firm—Peter C. Richardson; J. Trevor Lumb; A. Dean Olson

[57] ABSTRACT

Compounds of the formula

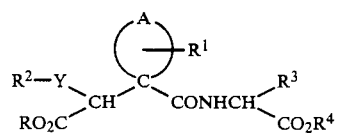

wherein A is a carbocyclic, saturated or unsaturated ring; $R^1$ is hydrogen or alkyl; R and $R^4$ are each alkyl, cycloalkyl, benzyl or a readily hydrolyzable ester group; Y is a bond or a straight or branch alkylene; $R^2$ is hydrogen, aryl, heterocyclic, $R^6CONR^5$, $R^7NR^5CO$, $R^7NR^5SO_2$—or $R^8SO_2NR^5$—where $R^5$ is hydrogen, alkyl or aralkyl; $R^6$ is alkyl, aryl, aralkyl, heterocyclic, heterocyclylalkyl or a group of the formula

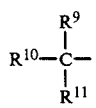

where $R^9$ is hydrogen, hydroxy, alkoxy, alkyl, hydroxyalkyl, aralkyl, alkylene, heterocyclic, heterocyclylalkyl, $R^{12}CONH$—, $R^{12}SO_2NH$— or $(R^{13})_2N$—; $R^{10}$ and $R^{11}$ are each hydrogen or alkyl; or $R^{10}$ is hydrogen and $R^{11}$ is aminoalkyl, imidazolylmethyl, aryl, aralkyl, aralkoxyalkoxy, hydroxyalkyl or methylthioalkyl; or $R^{10}$ and $R^{11}$ together with the carbon to which they are attached form a carbocyclic or heterocyclic ring optionally substituted by amino, alkanoyl or aroyl; $R^{12}$ is alkyl, cycloalkyl, aryl, aralkyl, heterocyclic or heterocyclylalkyl; each $R^{13}$ is hydrogen, alkyl, aralkyl or both $R^{13}$ together with the nitrogen to which they are attached form a heterocyclic ring; $R^7$ is alkyl, aryl, aralkyl, heterocyclic, heterocyclylalkyl or a group

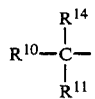

where $R^{10}$ and $R^{11}$ are as defined and $R^{14}$ is $(R^{13})_2NCO$, $R^{12}OCH_2$— or $R^{15}OCO$, where $R^{12}$ and $R^{13}$ are as defined and $R^{15}$ is alkyl, cycloalkyl or aralkyl; and $R^8$ is alkyl, aryl, aralkyl, heterocyclic or heterocyclylalkyl; $R^3$ is a group

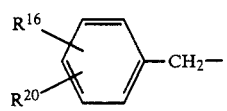

where $R^{16}$ is hydrogen, halo, hydroxy, alkoxy, cycloalkoxy, alkenyloxy, alkoxycarbonyloxy, cycloalkoxycarbonylalkoxy or alkyl $SO_2NH$—; and $R^{20}$ is hydrogen, alkyl, alkoxy, alkanoyl or halo; or $R^3$ is 3-indolylmethyl or 3-indazolylmethyl, each optionally substituted in the benzenoid ring by alkyl, alkoxy, hydroxy or trifluoromethyl as antihypertensive agents.

14 Claims, No Drawings

CYCLOALKYL-SUBSTITUTED GLUTARAMIDE ANTIHYPERTENSIVE AGENTS

BACKGROUND OF THE INVENTION

This invention relates to a series of cycloalkyl-substituted glutaramide derivatives which are antihypertensive agents having utility in the treatment of various cardiovascular disorders, including hypertension and heart failure.

According to the specification of our European patent application No. 274234, we disclose certain cycloalkyl-substituted glutaramide derivatives which are inhibitors of the zinc dependent neutral endopeptidase E.C.3.4.24.11 and which are thereby able to potentiate the biological effects of atrial natriuretic factor and in particular, are natriuretic, antihypertensive and diuretic agents of value in the treatment of various cardiovascular disorders.

The compounds of the present invention are also inhibitors of the enzyme E.C.3.4.24.11 and, in addition, they are also able to inhibit angiotensin converting enzyme, a further enzyme which is involved in the control of blood pressure. The compounds thus have a dual pharmacological action through inhibiting two key enzymes involved in blood pressure control which makes them particularly useful in the treatment of various forms of hypertension and associated cardiovascular disorders, e.g. congestive heart failure and glaucoma.

SUMMARY OF THE INVENTION

The compounds are of the formula:

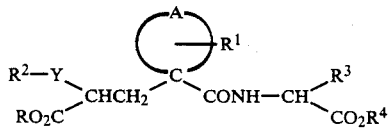

(I)

wherein:

A completes a 5 or 6 membered carbocyclic ring which may be saturated or monounsaturated;

$R^1$ is H or $C_1-C_4$)alkyl;

R and $R^4$ are each independently H, ($C_1-C_6$)alkyl,($C_3-C_7$)cycloalkyl, benzyl, or an alternative biolabile ester-forming group;

Y is either a direct bond or an alkylene group of from 1 to 6 carbon atoms which may be straight or branched chain;

$R^2$ is H, aryl, heterocyclyl, $R^6CONR^5$—, $R^7NR^5CO$—, $R^7NR^5SO_2$ or $R^8SO\ NR^5$—, with the proviso that Y is not a direct bond when $R^2$ is H, aryl or heterocyclyl;

wherein $R^5$ is H, or aryl($C_1-C_6$)alkyl;

$R^6$ is ($C_1-C_6$)alkyl, aryl, aryl($C_1-C_6$)alkyl, heterocyclyl, heterocyclyl($C_1-C_6$)alkyl or a group of the formula:

wherein $R^9$ is H, OH, ($C_1-C_6$)alkoxy, ($C_1-C_6$)alkyl, hydroxy($C_1-C_6$)alkyl, aryl($C_1-C_6$)alkyl, ($C_2-C_6$)alkenyl, heterocyclyl, heterocyclyl($C_1-C_6$)alkyl, $R^{12}CONH$—, $R^{12}SO_2NH$— or $(R^{13})_2N$—;

$R^{10}$ and $R^{11}$ are each independently H or ($C_1-C_6$)alkyl; or is H and $R^{11}$ is amino($C_1-C_6$)alkyl, imidazolylmethyl, aryl, aryl ($C_1-C_6$)alkyl, aryl($C_1-C_6$)alkoxy($C_1-C_6$)alkoxy, hydroxy )alkyl or methylthio($C_1-C_6$)alkyl; or the two groups $R^{10}$ and $R^{11}$ are joined together to form, with the carbon atom to which they are attached, a 3 to 6 membered carbocyclic ring or a pyrrolidine or piperidine ring which may optionally be substituted by amino, ($C_2-C_4$)alkanoyl or aroyl;

$R^{12}$ is ($C_1-C_6$)alkyl, ($C_3-C_7$)cycloalkyl, aryl, aryl(-$C_1-C_6$)alkyl, heterocyclyl or heterocyclyl )alkyl;

each $R^{13}$ is H, or the two groups each $R^{13}$ is H, ($C_1-C_6$)alkyl, aryl($C_1-C_6$)alkyl or the two groups $R^{13}$ are taken together to form, with the nitrogen to which they are attached, a pyrrolidinyl, piperidino, morpholino, piperazinyl or N-($C_1-C_4$)alkyl-piperazinyl group;

$R^7$ is ($C_1-C_6$)alkyl, aryl, aryl($C_1-C_6$)alkyl, heterocyclyl, heterocyclyl($C_1-C_6$)alkyl or a group of the formula:

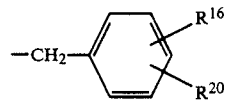

wherein $R^{10}$ and $R^{11}$ are as previously defined and $R^{14}$ is $(R^{13})_2NCO$—, $R^{12}OCH_2$— or $R^{15}OCO$, wherein $R^{12}$ and $R^{13}$ are as previously defined and $R^{15}$ is ($C_1-C_6$)alkyl, $C_3-C_7$)cycloalkyl or aryl($C_1-C_6$)alkyl; and $R^8$ is ($C_1-C_6$)alkyl, aryl, aryl($C_1-C_6$)alkyl, $R^3$ is a group of the formula:

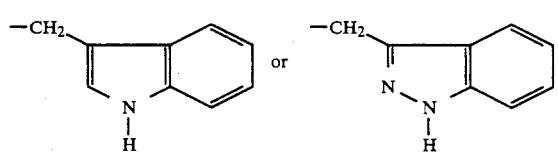

wherein $R^{16}$ is H, halo, 4-OH, 4-($C_1-C_6$ alkoxy), 4-($C_3-C_7$ cycloalkoxy),4-($C_2-C_6$ alkenyloxy). 4-alkoxy)-carbonyloxy], 4-[($C_3-C_7$ cycloalkoxy)carbonyloxy], or 3-($C_1-C_4$ alkyl)$SO_2NH$—; and is H,($C_1-C_4$)alkyl, ($C_1-C_4$)alkoxy, ($C_2-C_8$)alkanoyl or halo; or $R^3$ is a group of the formula:

wherein said groups may optionally be substituted in the fused benzene ring by($C_1-C_4$)alkyl, ($C_1-C_4$)alkoxy, OH, halo or $CF_3$; and pharmaceutically acceptable salts thereof and bioprecursors therefor.

In the above definition, unless otherwise indicated, alkyl groups having three or more carbon atoms may be straight or branched-chain. The term aryl as used herein means an aromatic hydrocarbon group such as phenyl or naphthyl which may optionally be substituted with, for example, one or more OH, CN, $CF_3$, $C_1-C_4$ alkyl, $C_1-C_4$ alkoxy, halo, carbamoyl, aminosulphonyl, amino, mono or di($C_1-C_4$ alkyl) amino or ($C_1-C_4$ alkanoyl)amino groups. Halo means fluoro, chloro, bromo or iodo.

The term heterocyclyl means a 5 or 6 membered nitrogen, oxygen or sulphur containing heterocyclic group which, unless otherwise stated, may be saturated or unsaturated and which may optionally include a further oxygen or one to three nitrogen atoms in the ring and which may optionally be benzofused or substituted with for example, one or more halo, $C_1$-$C_4$ alkyl, hydroxy, carbamoyl, benzyl, oxo, amino or mono or di-($C_1$-$C_4$ alkyl)amino or ($C_1$-$C_4$ alkanoyl)amino groups. Particular examples of heterocycles include pyridyl, pyrazinyl, pyrimidinyl, pyridazinyl, pyrrolyl. piperidino, imidazolyl, pyrazolyl, triazolyl, tetrazolyl, furanyl, tetrahydrofuranyl, tetrahydropyranyl, dioxanyl, thienyl, oxazolyl, isoxazolyl, thiazolyl, indolyl, isoindolinyl, quinolyl, quinoxalinyl, quinazolinyl and benzimidazolyl, each being optionally substituted as previously defined.

The compounds of formula (I) may contain several asymmetric centres and thus they can exist as enantiomers and diastereomers. The invention includes both the separated individual isomers as well as mixtures of isomers.

The pharmaceutically acceptable salts of the compounds of formula (I) containing an acidic centre are those formed with bases which form non-toxic salts. Examples include the alkali or alkaline earth metal salts such as the sodium, potassium or calcium salts or salts with amines such as diethylamine. Compounds having a basic centre can also for ⓒacid addition salts with pharmaceutically acceptable acids. Examples include the hydrochloride, hydrobromide, sulphate or bisulphate, phosphate or hydrogen phosphate, acetate, citrate, fumarate, gluconate, lactate, maleate, succinate, tartrate tosylate and lauryl sulphate salts.

The term bioprecursor in the above definition means a pharmaceutically acceptable biologically degradable derivative of the compound of formula (I) which, upon administration to an animal or human being, is converted in the body to produce a compound of the formula (I). Examples include biolabile ester derivatives and amide or amino acid derivatives of the compounds of formula I.

A preferred group of compounds of the formula (I) are those wherein A is $(CH_2)_4$ and $R^1$ is H, i.e. compounds of the formula (II) wherein R, $R^2$, $R^3$ and $R^4$ are as previously defined for formula (1):

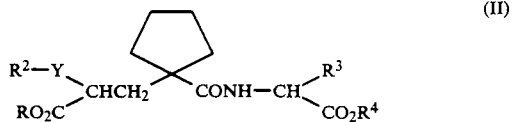

(II)

Also preferred are those compounds of formulae (I) and (II) wherein R and $R^4$ are both H (diacids) as well as biolabile mono and di-ester derivatives thereof wherein one or both of R and $R^4$ is a biolabile ester-forming group.

The term biolabile ester-forming group is well understood in the art as meaning a group which provides an ester which can be readily cleaved in the body to liberate the corresponding diacid of formula (I) wherein R and $R^4$ are both H. A number of such ester groups are well known, for example in the penicillin area or in the case of the ACE-inhibitor antihypertensive agents.

In the case of the compounds of formulae (I) and (II) such biolabile pro-drug esters are particularly advantageous in providing compounds of the formula (I) suitable for oral administration. The suitability of any particular ester-forming group can be assessed by conventional animal or in vitro enzyme hydrolysis studies. Thus, desirably for optimum effect, the ester should only be hydrolysed after absorption, accordingly, the ester should be resistant to hydrolysis by digestive enzymes before absorption but should be readily hydrolyzed by, for example, gut-wall, plasma or liver enzymes. In this way the active diacid is released into the bloodstream following oral absorption.

In addition to lower alkyl esters (particularly ethyl) and benzyl esters, alternative biolabile esters include alkanoyloxyalkyl esters, including alkyl, cycloalkyl and aryl substituted derivatives thereof, aroyloxyalkyl esters, arylesters, aralkylesters, haloalkyl esters and hydroxyalkyl esters including ketal derivatives thereof, wherein said alkanoyl or alkyl groups have from 1 to 8 carbon atoms and are branched or straight chain and said aryl groups are phenyl, naphthyl or indanyl optionally substituted with one or more $C_1$-$C_4$ alkyl, $C_1$-$C_4$ alkoxy or $C_1$-$C_4$ alkoxycarbonyl groups or halo atoms.

Thus examples of R and $R^4$ when they are biolabile ester groups include ethyl, indanyl, isopropyl, n-butyl, sec-butyl, t-butyl, cyclohexyl, benzyl, phenethyl, phenpropyl, acetonyl, glyceryl, pivaloyloxymethyl, 5-(4-methyl-1,3-dioxolene-2-onyl)methyl, cyclohexylmethyl, cyclohexylcarboxyethyl, cyclohexylacetoxyethyl, propionyloxyisobutyl, hexanoyloxyethyl, pentanoyloxyethyl, acetoxyethyl, acetoxybenzyl, pentanoyloxybenzyl, cyclohexyloxycarbonyloxyethyl, butyloxycarbonyloxyethyl, isobutyloxycarbonylethyl and ethoxycarbonyloxyethyl.

In one preferred aspect of the invention, the group $R^3$ is 4-hydroxybenzyl and the carbon atom to which it is attached is of (S) stereochemistry; the group $NHCH(R^3)CO_2R^4$ being derived from L-tyrosine. Also preferred are compounds wherein $R^3$ is 4-methoxybenzyl or 3-methanesulphonamidobenzyl.

In further aspects of the invention $R^2$ is H and Y is $(CH_2)_3$ or $R^2$ is phenyl and Y is $(CH_2)_2$.

In another aspect of the invention $R^2$ is $R^6CONR^5$ and Y is $CH_2$, $R^3$ is 4-hydroxybenzyl, 4-methoxybenzyl or 3-methane-sulphonamidobenzyl and $R^6$ is of formula $R^9R^{10}R^{11}C$—, wherein $R^9$ is $(R^{13})_2N$—, $R^{12}SO_2NH$— or $R^{12}CONH$—, $R^{10}$ is amino($C_1$-$C_6$)alkyl and $R^{11}$ is H. Particularly preferred are compounds of the formula (I) wherein Y is $CH_2$ and $R^2$ is $R^6CONH$— and $R^6CO$ is (S)-lysyl or $N^2$ substituted (S)-lysyl (wherein $R^9$ is $NH_2$, $R^{12}CONH$ or $R^{12}$ $SO_2NH$, $R^{10}$ is 4-aminobutyl and $R^{11}$ is H). Preferred substituents for $R^{12}$ are methyl and phenyl.

Particularly preferred individual compounds of the invention include N-[1-(2(S)-carboxy-3-(S)-lysylaminopropyl)-1-cyclopentanecarbonyl]-(S)-tyrosine, N- {1-[2(S)-carboxy-3-($N^2$-methanesulphonyl-(S)-lysylamino)propyl]-1-cyclopentanecarbonyl}-(S)-tyrosine, N-{1-[2(S)-carboxy-3-($N^2$-2-furoyl-(S)-lysylamino)propyl]-1-cyclopentanecarbonyl}-(S)-tyrosine, N-{1-[2-(S)-carboxy-3-($N^2$-acetyl-(S)-lysylamino)propyl]-1-cyclopentanecarbonyl}-(S)-4-methoxyphenylalanine, N-[1-(2-carboxy-3-(S)-lysylaminopropyl-1-cyclopentanecarbonyl]-3-methanesulphonamidophenylalanine, N-{1-[2-carboxy-3-($N^2$-methanesulphonyl-(S)-lysylamino)propyl]-1-cyclopentanecarbonyl}-3-methanesulphonamidophenylalanine, N-{1-[2-carboxy-3-($N^2$-acetyl-(S)-lysylamino)propyl]-1-cyclopentanecarbonyl}-(S)-3-methanesulphonamidophenylalanine, and N-{1-[2(S)-carboxy-3-(N²-phenylsulphonyl-(S)-lysylamino)propyl]-1-cyclopentanecarbonyl}-(S)-tyrosine, and salts and biolabile ester derivatives thereof.

DETAILED DESCRIPTION OF THE INVENTION

The compounds of formula (I) are prepared by a number of different processes:

(a) One procedure involves the synthesis of a partially protected cycloalkyl-substituted glutaric acid derivative which is coupled to an amino acid ester derivative to give the desired glutaramide. Any reactive groups in $R^2$ and $R^3$ may require protection during the coupling step and such Protecting groups are removed in the final stage of the process. The synthetic route is illustrated in the following reaction scheme wherein A and $R^1$ are as previously defined, $R^{2'}$ and $R^{3'}$ are as defined for $R^2$ and $R^3$ with any reactive groups therein protected if necessary and $R^{17}$ and $R^{18}$ are as defined for R and $R^4$ excluding H, or they are conventional carboxylic acid protecting

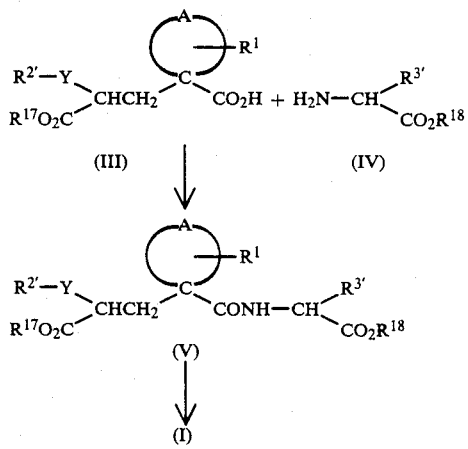

The reaction of the compounds of formula (III) and (IV) is achieved using conventional amide coupling techniques. Thus in one process the reaction is achieved with the reactants dissolved in an organic solvent, e.g. dichloromethane, using a diimide condensing agent, for example 1-ethyl-3-(dimethylaminopropyl)carbodiimide, or N,N'-dicyclohexylcarbodiimide, advantageously in the presence of 1-hydroxybenzotriazole and an organic base such as N-methylmorpholine. The reaction is generally complete after a period of from 12 to 24 hours at room temperature and the product is then isolated by conventional procedures, i.e. by washing with water or filtration to remove the urea byproduct and evaporation of the solvent. The product may be further purified by crystallization or chromatography, if necessary.

The compounds of formula (V) include compounds of formula (I) wherein R and $R^4$ are $C_1$-$C_6$ alkyl or benzyl.

The diesters of formula (V) are subsequently reacted to give the monoester or diacid derivatives of formula (I) wherein one or both of R and $R^4$ are H. The conditions used will depend on the precise nature of the groups $R^{17}$ and $R^{18}$ present in the compound of formula (V) and a number of variations are possible. Thus for example when both of $R^{17}$ and $R^{18}$ are benzyl, hydrogenation of the product will yield the diacid of formula (1) wherein R and $R^4$ are both H. Alternatively if one of $R^{17}$ and $R^{18}$ is benzyl and the other is alkyl, hydrogenation will yield a monoester product. This can then be hydrolysed, if desired, to again yield the diacid product. When one of $R^{17}$ and $R^{18}$ is t-butyl, treatment of the compound of formula (V) with trifluoroacetic acid or hydrogen chloride yields the corresponding acid. If some other carboxylic acid protecting group is used for $R^{17}$ or $R^{18}$ then clearly appropriate conditions for its removal must be employed in the final step to give the ester or diacid product of formula (I). For example when $R^{17}$ or $R^{18}$ is trimethylsilylethyl it may be removed by treatment with tetrabutylammonium fluoride. Any protecting groups present in $R^{2'}$ and $R^{3'}$ must also be removed and this may be performed concomitantly with removal of protecting groups present in $R^{17}$ $R^{18}$ and or as a separate step using procedures appropriate to the particular protecting group employed. Thus, for example when $R^{2'}$ contains a substituted or protected amino group (for example a benzylamino, dibenzylamino, benzyloxycarbonylamino or t-butyloxycarbonylamino group) the compounds may be converted to the free amines by hydrogenation or hydrolysis as appropriate.

(b) In an alternative process, compounds of the formula (I) wherein $R^2$ is $R^6CONR^5$— or $R^8SO_2NR^5$— are prepared by a process which involves reacting an amine of the formula:

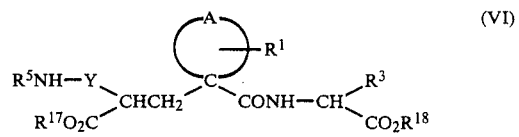

wherein A, Y, $R^1$, $R^3$, $R^5$, $R^{17}$ and are as previously defined; with a carboxylic acid or sulphonyl chloride of the formulae:

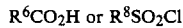

respectively, or a reactive derivative of the carboxylic acid, wherein $R^6$ and $R^8$ are as previously defined, and wherein any reactive groups therein are optionally protected, to yield for example a compound of the formula:

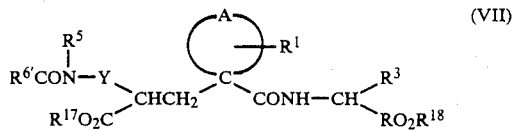

wherein $R^{6'}$ is as previously defined for $R^6$ with any reactive groups therein optionally protected; and subsequently removing any protecting groups, if present and, if desired hydrolysing the ester product to yield the compounds of formula (I) wherein R and $R^4$ are H.

Similarly, reaction with the sulphonyl chloride yields the corresponding sulphonamides.

The reaction of the amine of formula (VI) and compound of formula $R^6CO_2H$ or $R^8SO_2Cl$ is achieved using conventional amide coupling techniques as previously described or, in the case of the sulphonyl compounds, by reaction with the corresponding sulphonyl chloride. Subsequent removal of protecting groups is achieved using appropriate procedures as previously described.

The amines of formula (VI) are prepared following the same procedure outlined in process (a) above but using an acid of formula (III) wherein $R^{2'}$ is a protected amine of formula $R^{19}NR^5$— wherein $R^5$ is as previously defined and $R^{19}$ is an amino-protecting group.

Thus, in one variant of this process the coupling reaction with the amino acid derivative is achieved using a compound of formula (III) wherein $R^2$ is $R^{19}R^5N$— and $R^{19}$ and $R^5$ are both benzyl. Alternatively $R^{19}$ and $R^5$ are both S-α-methylbenzyl to enable the S-isomer of the compound of formula (V) to be isolated. Hydrogenation of the coupled product of formula (V) gives the amine of formula (VI) wherein $R^5$ is H. This is then reacted with, for example a protected lysine derivative of formula $R^6CO_2H$ (wherein $R^{6'}$ is $R^9R^{10}R^{11}C$—, $R^9$ is protected amino or $R^{12}CONH$—, $R^{12}SO_2NH$—, $R^{10}$ is N-protected-4-aminobutyl and $R^{11}$ is H), deprotection of the resulting product yields the corresponding product of formula (I) wherein $R^6CO$ is (S)-lysyl or $N^2$-substituted-(S)-lysyl.

(c) Compounds of the formula (I) wherein $R^2$ is $R^7NR^5CO$— or $R^7NR^5SO_2$ are prepared in an exactly analogous manner to that described above but starting with a carboxylic acid or sulphonic acid of the formula:

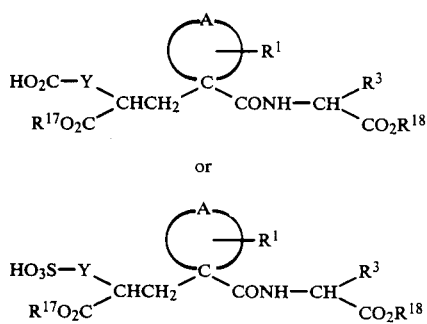

or wherein A, Y, $R^1$, $R^3$, $R^{17}$ and $R^{18}$ are as previously defined, and reacting with an amine of the formula $R^7R^5NH$, followed by removal of protecting groups if present and, if desired, hydrolysing or hydrogenating the ester product to yield the compounds of formula (I) wherein R and $R^4$ are H.

(d) In s further variant of these processes, the coupling is achieved using s compound of the formula (IV) wherein $R^3$ is of formula:

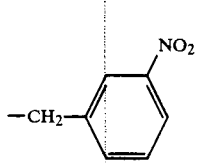

Subsequent reduction of the nitro group, followed by sulphonation of the product with a sulphonyl halide of the formula $(C_1-C_4)$alkyl $SO_2Cl$ yields the corresponding compound of formula (V) wherein $R^{3'}$ is

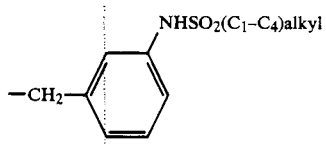

Compounds of the formula (I) wherein one or both of R and $R^4$ is a biolabile ester-forming group are prepared following similar procedures to those outlined above using the appropriate ester group for R or $R^4$.

As well as removing any protecting group which may be present in $R^2$, a number of chemical transformation reactions are possible on the final mono-ester or diacid products as previously described. In each case the product may be obtained as the free carboxylic acid or it may be neutralized with an appropriate base and isolated in salt form.

Appropriate coupling and protecting methods for all of the above steps and alternative variations and procedures will be well known to those skilled in the art by reference to appropriate text books and to the examples provided hereafter.

The starting spiro-substituted glutaric acid mono esters of formula III may be prepared as described in our European patent application No. 274234. The amino acid esters of formula (IV) are generally known compounds which are either commercially available or they may be prepared by standard methods in accordance with literature precedents.

As previously mentioned, the compounds of the invention are Potent inhibitors of the neutral endopeptidase (E.C.3.4.24.11). This enzyme is involved in the breakdown of a number of peptide hormones including, in particular the breakdown of atrial natriuretic factor (ANF). Thus, the compounds of the invention, by preventing the degradation of ANF by endopeptidase E.C.3.4.24.11, can potentiate its biological effects and the compounds are thus diuretic, natriuretic and antihypertensive agents of utility in a number of disorders including hypertension, heart failure, angina, renal insufficiency, premenstrual syndrome, cyclical oedema, Menieres disease, hyperaldosteroneism (primary and secondary) and hypercalciuria. In addition, because of their ability to potentiate the effects of ANF the compounds have utility in the treatment of glaucoma. As a further result of their ability to inhibit the neutral endopeptidase E.C.3.4.24.11 the compounds of the invention may have activity in other therapeutic areas including for example the treatment of asthma, inflammation, pain, epilepsy, affective disorders, dementia and geriatric confusion, obesity and gastrointestinal disorders (especially diarrhea and irritable bowel syndrome), the modulation of gastric acid secretion and the treatment of hyperreninaemia.

Activity against neutral endopeptidase E.C.3.4.24.11 is assessed using a procedure based on the assay described by J. T. Gafford, R. A. Skidgel, E. G. Erdos and L. B. Hersh, *Biochemistry*, 1983, 32, 3265–3271The method involves determining the concentration of compound required to reduce by 50% the rate of release of radiolabelled hippuric acid from hippuryl-L-phenylalanyl-L-arginine by a neutral endopeptidase preparation from rat kidney.

As previously mentioned, the compounds of the invention are also inhibitors of angiotensin converting enzyme. As such they are useful in treating a further variety of conditions for which ACE inhibitors are known to be useful including limitation of ischaemic damage to the myocardium, protection of the kidney against hyperfiltration damage, prevention or reversal of left ventricular hypertrophy, memory enhancement, control of cognitive function, dementia, and preventing reocclusion following coronary angioplasty or coronory artery bypass surgery. Their activity against this enzyme is assessed using a modified procedure based on the assay described by Rohrbach, M. S., Anal. Biochem., 1978, 84, 272. The method involves determining the concentration of compound required to reduce by 50% the extent of release of radiolabelled hippuric acid from hippuryl-L-histidyl-L-leucine by angiotensin converting enzyme isolated from the rat kidney.

Inhibitory activity is also measured in vivo following intravenous injection to anesthetized rats using the methods described by I. L. Natoff et al, Journal of Pharmacological Methods, 1981, 5, 305 and by D. M. Gross et al, J. Pharmacol. Exp. The., 1981, 216, 552. The dose of inhibitor required to reduce the presser response produced by intravenous injection of angiotensin I (50 ng bolus) by 50% is determined.

The activity of the compounds as diuretic agents is determined by measuring their ability to increase urine output and sodium ion excretion in saline loaded conscious mice. In this test, male mice (Charles River CD1, 22-28 g) are acclimatized and starved overnight in metabowls. The mice are dosed intravenously via the tail vein, with the test compound dissolved in a volume of saline solution equivalent to 2.5% of body weight. Urine samples are collected each hour for two hours in pre-weighed tubes and analyzed for electrolyte concentration. Urine volume and sodium, ion concentration from the test animals are compared to a control group which received only saline.

The antihypertensive activity of the compounds is evaluated by measuring the fall in blood pressure following oral or intravenous administration to salt depleted, diuretic primed, spontaneously hypertensive rats, salt depleted renally hypertensive dogs, or DOCA/salt hypertensive rats.

For administration to man in the curative or prophylactic treatment of hypertension, congestive heart failure or renal insufficiency, oral dosages of the compounds will generally be in the range of from 3-1500 mg daily for an average adult patient (70 kg). Thus for a typical adult patient, individual tablets or capsules contain from 1 to 500 mg of active compound, in a suitable pharmaceutically acceptable vehicle or carrier for administration singly, or in multiple doses, once or several times a day. Dosages for intravenous administration would typically be within the range 1 to 500 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical, practice. For example, they may be administered orally in the form of tablets containing such excipients as starch or lactose, or in capsules or ovules either alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The compounds may be co-administered with other agents as may be beneficial for the control of blood pressure or the treatment of cardiac conditions or renal insufficiency. Thus for example they may be co-administered with digitalis or another cardiac-stimulant drug or with an alpha-blocker, beta-blocker, exogenous ANF or with a potassium channel activator or another diuretic agent as shall be determined by the physician as appropriate to the particular patient or disease state.

Thus in a further aspect the invention provides a pharmaceutical composition comprising a compound of the formula (I) or (II), or a pharmaceutically acceptable salt thereof or bioprecursor therefor, together with a pharmaceutically acceptable diluent or carrier.

The invention also includes a compounds of the formula (I) or (II), or a pharmaceutically acceptable salt thereof or bioprecursor therefor, for use in medicine, in particular in the treatment of hypertension, congestive heart failure or renal insufficiency in a human being.

The preparation of the compounds of the invention and of intermediates for use in their preparation is illustrated by the following Examples.

EXAMPLE 1

N-[1-(2-t-Butyloxycarbonyl-3-dibenzylaminopropyl)-1-cyclopentane-carbonyl]-O-t-butyl-(S)-tyrosine-t-butyl ester To an ice cold solution of 1-(2-t-butyloxycarbonyl-3-dibenzylaminopropyl)-1-cyclopentane carboxylic acid (12.7 g, 27 mmole) in dry dichloromethane (100 ml) was added 1-hydroxybenztriazole (4.2 g,.31 mmole), and 1-ethyl-3-(dimethylaminopropyl)-carbodiimide (7 g, 36 mmole) and the resulting solution stirred at 0° C. for 30 minutes. To this solution was added 0-t-butyltyrosine t-butyl ester (8.4 g, 28.6 mmole) and N-methylmorpholine (5.25 g, 52 mmole) and the solution allowed to stand overnight at room temperature. The solvent was evaporated under reduced pressure and the resultant mobile oil was dissolved in methylene chloride and washed with water (2 x ), 2M hydrochloric acid and saturated aqueous sodium bicarbonate (1 x) dried (MgSO4), and the solution filtered and evaporated to yield the crude product as a gum. Recrystallization from n-hexane gave the title compound as a solid (13 g, 69%), m.p. 82–87° C. A further batch of material was obtained by evaporation of the supernatant liquors and further recrystallisation. Found: C,74.12; H,8.69; N,3.87. C45H62N2O6 requires C,74.34; H,8.59; N,3.85%.

EXAMPLES 2–38

The following compounds were prepared following the general procedure of Example 1 starting with the appropriate carboxylic acid and coupling to the appropriate aminoacid ester. Unless otherwise stated the group —NHCH(R$^3$)CO$_2$R$^4$ is derived from the naturally occurring amino acids having S stereochemistry.

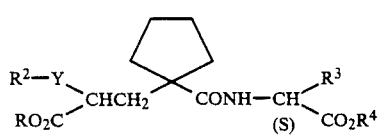

Examples 33–35 are the separated isomers having S,S stereochemistry.

| Example No. | R | R²Y | R³ | R⁴ | Analysis % (Theoretical in brackets) | | |
|---|---|---|---|---|---|---|---|
| | | | | | C | H | N |
| 2 | (CH₃)₃C— | (C₆H₅CH₂)₂NCH₂— | —CH₂—C₆H₄—OH (4-) | (CH₃)₃C— | gum, Rf. 0.81 (silica, ethyl acetate, toluene; 1:1) | | |
| 3 | (CH₃)₃C— | (C₆H₅CH₂)₂NCH₂— | —CH₂—C₆H₄—OC(CH₃)₃ (4-) | C₂H₅— | 73.24 (73.89 | 8.32 8.37 | 3.82 4.01) |
| 4 | (CH₃)₃C— | (C₆H₅CH₂)₂NCH₂— | —CH₂—C₆H₅ | (CH₃)₃C— | gum, Rf 0.91 (silica; ethylacetate, toluene; 1:1) | | |
| 5 | (CH₃)₃C— | (C₆H₅CH₂)₂NCH₂— | —CH₂—C₆H₄—NO₂ (3-) (R,S) | C₂H₅— | 69.74 (69.73 | 7.42 7.35 | 6.01 6.25) |
| 6 | (CH₃)₃C— | (C₆H₅CH₂)₂NCH₂— | —CH₂—C₆H₄—OCH₃ (4-) | C₂H₅— | 73.14 (73.34 | 7.98 7.84 | 4.26 4.32) |
| 7 | C₆H₅CH₂— | CH₃CH₂CH₂— | —CH₂—C₆H₄—NO₂ (3-) (R,S) | C₆H₅CH₂— | gum, Rf 0.37 (silica, CH₂Cl₂, CH₃OH; 98:2) | | |
| 8 | C₆H₅CH₂— | CH₃CH₂CH₂— | —CH₂—C₆H₄—OCH₃ (4-) | H | gum, Rf 0.12 (silica, CH₂Cl₂, CH₃OH; 98:2) | | |
| 9 | C₆H₅CH₂— | CH₃CH₂CH₂— | —CH₂—C₆H₄—OH (4-) | CH₃— | 70.04 (68.87 | 7.53 7.54 | 2.72 2.65)[1] |
| 10 | C₆H₅CH₂— | CH₃CH₂CH₂— | —CH₂—C₆H₄—OH (4-) | C₂H₅ | 68.46 (68.87 | 7.48 7.54 | 2.91 2.65)[1] |
| 11 | C₆H₅CH₂— | CH₃CH₂CH₂— | —CH₂-(indol-3-yl) | CH₃— | 69.15 (69.38 | 7.22 7.51 | 5.23 5.22) |
| 12 | C₆H₅CH₂— | CH₃CH₂CH₂— | —CH₂—C₆H₅ | C₂H₅— | 72.28 (72.33 | 7.87 7.99 | 2.77 2.81) |

-continued

| Example No. | R | R²Y | R³ | R⁴ | Analysis % (Theoretical in brackets) C | H | N |
|---|---|---|---|---|---|---|---|
| 13 | C₆H₅CH₂ | CH₃CH₂CH₂— | 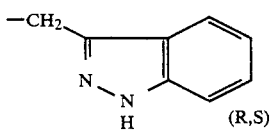 (R,S) | H | gum Rf 0.52 (silica; CH₂Cl₂, CH₃OH CH₃CO₂H; 90:10:1) | | |
| 14 | C₆H₅CH₂— | C₆H₅CH₂CH₂— | 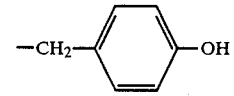 | CH₃— | 72.86 (73.22 | 7.57 7.05 | 2.47 2.51) |
| 15 | C₆H₅CH₂— | C₆H₅CH₂CH₂— | 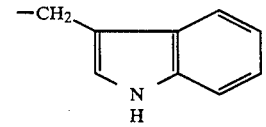 | CH₃— | 71.89 (72.26 | 7.05 6.76 | 7.53 7.22) |
| 16 | C₆H₅CH₂— | C₆H₅CH₂CH₂— | 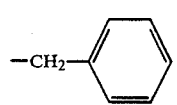 | C₆H₅CH₂— | 75.14 (75.70 | 6.86 6.84 | 4.62 4.53) |
| 17 | C₆H₅CH₂— | CH₃(CH₂)₂— | 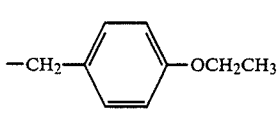 | —CH₂CH₃ | 71.10 (71.48 | 8.10 8.06 | 2.21 2.60) |
| 18 | C₆H₅CH₂ | CH₃(CH₂)₂— | 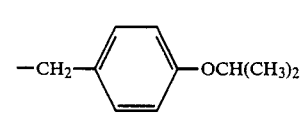 | —CH₂CH₃ | 71.78 (71.84 | 8.45 8.22 | 2.50 2.54) |
| 19 | (CH₃)₃C— | (C₆H₅CH₂)₂NCH₂— | 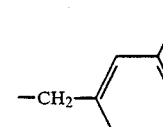 | —CH₂CH₃ | 66.13 (66.40 (dihydrate) | 7.37 7.41 | 5.49 5.80) |
| 20 | (CH₃)₃C— | (C₆H₅CH₂)₂NCH₂— | 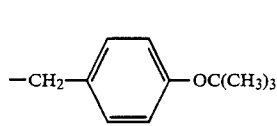 | 3-pentyl | 73.48 (73.70 (0.125 mole CH₂Cl₂) | 8.66 8.62 | 3.79 3.73) |
| 21 | (CH₃)₃C— | (C₆H₅CH₂)₂NCH₂— | 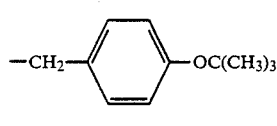 | cyclohexyl | 74.36 (74.96 | 8.77 8.56 | 3.95 3.72) |
| 22 | (CH₃)₃C— | (C₆H₅CH₂)₂NCH₂— | 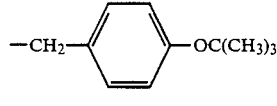 | 2,4-dimethyl-pentyl | Rf 0.69 (toluene, EtOAc, 1:1) | | |
| 23 | (CH₃)₃C— | (C₆H₅CH₂)₂NCH₂— | 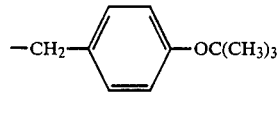 | 3-phenpropyl | 74.51 (74.79 (0.2 mole CH₂Cl₂) | 8.00 8.05 | 3.81 3.47) |
| 24 | (CH₃)₃C— | (C₆H₅CH₂)₂NCH₂— | 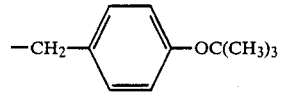 | 4-t-butyl-cyclohexyl | Rf 0.81 (diethylether, petrol; 1:1) | | |

-continued

| Example No. | R | R²Y | R³ | R⁴ | Analysis % (Theoretical in brackets) | | |
|---|---|---|---|---|---|---|---|
| | | | | | C | H | N |
| 25 | (CH₃)₃C— | (C₆H₅CH₂)₂NCH₂— | —CH₂—C₆H₄—OCH₂C₆H₅ | 2,4,6-tri-methylphenyl | 76.93 (77.34 | 7.84 7.59 | 3.49 3.40) |
| 26 | CH₃CH₂— | (C₆H₅CH₂)₂NCH₂— | —CH₂—C₆H₄—OC(CH₃)₃ | (CH₃)₃C— | 72.76 (73.89 | 8.36 8.37 | 4.03 4.01) |
| 27 | C₆H₅(CH₂)₃— | (C₆H₅CH₂)₂NCH₂— | —CH₂—C₆H₄—OC(CH₃)₃ | (CH₃)₃C— | Rf 0.6 (toluene, EtOAc; 1:1) | | |
| 28 | CH₃CH₂— | (C₆H₅CH₂)₂NCH₂— | —CH₂—C₆H₄—OH | CH₃CH₂— | 72.28 (72.37 | 7.73 7.55 | 4.44 4.56 |
| 29 | (CH₃)₃C— | (C₆H₅CH₂)₂NCH₂— | —CH₂—C₆H₄—OH | CH₃CH₂— | 72.83 (72.87 | 7.83 7.84 | 4.54 4.36) |
| 30 | (CH₃)₃C— | (C₆H₅CH₂)₂NCH₂— | —CH₂—C₆H₄—OH | cyclo-hexyl | 73.57 (73.55 (0.29 mole H₂O) | 8.29 8.12 | 3.90 3.99) |
| 31 | (CH₃)C— | (C₆H₅CH₂)NCH₂— | —CH₂—C₆H₄—OH | cyclo-heptyl | 74.03 (74.33 | 8.29 8.22 | 3.94 3.94) |
| 32 | (CH₃)₃Si(CH₂)₂— | (C₆H₅CH₂)₂NCH₂— | —CH₂—C₆H₄—OC(CH₃)₃ | (CH₃)₃C— | 64.58 (65.04 | 9.21 9.21 | 4.70 4.74) |
| 33 | (CH₃)₃Si(CH₂)₂— | C₆H₅CH(S)(CH₃)N(S)(CH(CH₃)C₆H₅)CH₂— | —CH₂—C₆H₄—OC(CH₃)₃ | (CH₃)₃C— | 72.03 (72.14 | 9.08 8.83 | 3.76 3.51 |
| 34 | (CH₃)₃Si(CH₂)₂— | C₆H₅CH(S)(CH₃)N(S)(CH(CH₃)C₆H₅)CH₂— | —CH₂—C₆H₄—NHSO₂CH₃ | (CH₃)₃C— | 66.00 (65.89 | 7.97 7.99 | 5.30 5.12) |
| 35 | (CH₃)₃C— | C₆H₅CH(S)(CH₃)N(S)(CH(CH₃)C₆H₅)CH₂— | —CH₂—C₆H₄—OC(CH₃)₃ | CH₃CH₂— | 74.02 (74.34 | 8.34 8.59 | 4.08 3.85) |
| 36 | C₆H₅CH₂— | CH₃CH₂CH₂— | —CH₂—C₆H₃(Cl)—OH (R,S) | CH₃CH₂— | Rf 0.82 (CH₂Cl₂, CH₃OH, AcOH; 90:10:1) | | |

-continued

| Example No. | R | R²Y | R³ | R⁴ | Analysis % (Theoretical in brackets) | | |
|---|---|---|---|---|---|---|---|
| | | | | | C | H | N |
| 37 | $C_6H_5CH_2-$ | $CH_3CH_2CH_2-$ | −CH₂−(2-CH₃, 6-NHSO₂CH₃ phenyl) | R,S | H | 61.08 (60.99 | 7.31 7.12 | 4.20 4.74) |
| 38 | $C_6H_5CH_2-$ | $CH_3CH_2CH_2-$ | −CH₂−(2-H₃CCO, 6-NHSO₂CH₃ phenyl) | R,S | H | Rf 0.50 ($CH_2Cl_2$, $CH_3OH$, AcOH; 90:10:1) | | |

(1) 0.2 mole $CH_2Cl_2$

EXAMPLE 39

1-(2-Benzyloxycarbonylpentyl)-1-cyclopentanecarbonyl-3-methanesulphonamido-(R,S)-phenylalanine benzyl ester (a) A mixture of 1-(2-benzyloxycarbonylpentyl)-1-cyclopentanecarbonyl-3-nitro-(R,S)-phenylalanine benzyl ester (3 g, 499 mmole), zinc dust (7 g, 107 mmole) and ammonium chloride (7 g, 131 mmole) in methanol (200 ml) was heated under reflux for 24 hours. The solvent was removed under reduced pressure, the residue gasified to pH 12 by the addition of 2N sodium hydroxide solution and the resulting mixture extracted with ethyl acetate (3×75 ml). The combined extracts were washed with brine, dried (MgSO₄) and the solvent evaporated to yield 1-(2-benzyloxycarbonylpentyl)-1-cyclopentanecarbonyl-3-amino-(R,S)-phenylalanine benzyl ester as an oil (2.36 g).

(b) Methane sulphonyl chloride (0.56 g, 0.49 mmole), and pyridine (0.039 g, 0.49 mmole) were added to a solution of the amine from part (a) above (0.236 g, 0.41 mmole) in dichloromethane (5 ml) and the solution stirred at room temperature for 1 hour. The solution was diluted with dichloromethane (50 ml), washed with citric acid (1N, 3×5 ml), saturated aqueous sodium bicarbonate solution (3×5 ml) and water, dried and the solvent evaporated under reduced pressure. The resulting oil was chromatographed on silica gel eluting with dichloromethane followed by a mixture of dichloromethane and methanol (98:2) to give the title product as a viscous oil (0.17 g).

EXAMPLE 40

1-(2-t-Butyloxycarbonyl-3-dibenzylaminopropyl)-1-cyclopentane-carbonyl-3-methanesulphonamido-(R,S)-phenylalanine ethyl ester The procedure of Example 39 was followed starting with 1-(2-t-butyloxycarbonyl-3-dibenzylaminopropyl)-1-cyclopentane-carbonyl-3-nitro-(R,S)-phenylalanine ethyl ester (from Example 5) to yield the title compound as an oil (3.17 g, 72%).

EXAMPLE 41

1-(2-Carboxypentyl)-1-cyclopentanecarbonyl-3-methane-sulphonamido-(R,S)-phenylalanine A solution of 1-(2-benzyloxycarbonylpentyl)-1-cyclopentane-carbonyl-3-methanesulphonamido-(R,S)-phenylalanine benzyl ester (0.16 g) in ethanol (5 ml) and water (1 ml) was hydrogenated over palladium on charcoal catalyst (10%, 0.016 mg) at a pressure of 30 p.s.i. (2 bar) and room temperature for 3 hours. The catalyst was removed by filtration and the solvent evaporated to yield a foam. Trituration with diethyl ether followed by drying under vacuum gave the title product as a glass (0.45 g). Found: C,55.37; H,6.97; N,5.69. $C_{22}N_{32}N_2O_7 \cdot 0.5$ $H_2O$ requires C,55.33; H,6.96; N,5.87%.

EXAMPLE 42-47

The following compounds were prepared by catalytic hydrogenation of the corresponding benzyl ester following the procedure of Example 41.

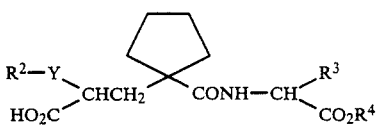

| Example No. | R²Y | R³ | R⁴ | Analysis % (Theoretical in brackets) C / H / N |
|---|---|---|---|---|
| 42 | $CH_3CH_2CH_2-$ | $-CH_2-C_6H_4-OCH_3$ | H | 63.11 7.63 3.91 (63.06 7.83 3.34) (0.75 mole $H_2O$) |
| 43 | $CH_3CH_2CH_2-$ | $-CH_2-C_6H_4-OH$ | $C_2H_5-$ | 65.58 8.18 2.92 (65.85 7.93 3.34) |
| 44 | $CH_3CH_2CH_2-$ | $-CH_2-$(indazolyl) | H | 61.40 7.02 9.43 (60.96 7.20 9.09) (hydrate) |
| 45 | $CH_3CH_2CH_2-$ | $-CH_2-$(2-CH₃-6-NHSO₂CH₃-phenyl) R,S | H | 53.88 7.24 5.71 (54.20 7.32 5.50) (1.5 mole $H_2O$) |
| 46 | $CH_3CH_2CH_2-$ | $-CH_2-$(2-CH₃CO-6-NHSO₂CH₃-phenyl) R,S | H | 55.60 7.29 5.49 (55.47 6.79 5.39) (0.5 mole $H_2O$) |

EXAMPLE 47

N-[1-(2-Carboxy-4-phenylbutyl)-1-cyclopentanecarbonyl]-(S)-tyrosine

A solution of N-[1-(2-benzyloxycarbonyl-4-phenylbutyl))-1-cyclopentanecarbonyl-(S)-tyrosine methyl ester (0.8 g, 1.47 mmole) in methanol (8 ml) was hydrogenated over 10% palladium on charcoal (100 mg) under an atmosphere of hydrogen (25 p.s.i., 1.7 bar) at room temperature for 2 hours. The reaction mixture was filtered through an 'arbacel' pad and evaporated to dryness. The residue was re-dissolved in aqueous sodium hydroxide (0.5M, 10 ml) and stirred at room temperature for 2 hours. The reaction mixture was washed with diethyl ether and acidified to pH 1 with aqueous hydrochloric acid (10%). The aqueous phase was extracted with diethyl ether (x2) and the combined organic phases dried ($Na_2SO_4$) and evaporated to yield the title product as a foam (0.27 g, 40%). Found: C,67.24; H,6.85; N,3.26. $C_{26}H_{31}NO_6 \cdot 0.25$ $H_2O$ requires C,67.54; H,6.97; N,3.03%.

EXAMPLES 48–55

The following compounds were prepared by catalytic hydrogenation followed by hydrolysis of the resulting mono ester following the procedure of Example 47.

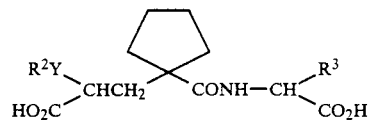

| Example No. | R²Y— | R³ | Analysis % (Theoretical in brackets) C / H / N |
|---|---|---|---|
| 48 | $CH_3CH_2CH_2-$ | $-CH_2-$(indolyl) | 66.28 7.62 6.51 (66.64 7.30 6.76) |
| 49 | $CH_3CH_2CH_2-$ | $-CH_2-$phenyl | 66.30 7.74 3.80 (66.38 7.82 3.69) |

-continued

| Example No. | R²Y— | R³ | Analysis % (Theoretical in brackets) | | |
|---|---|---|---|---|---|
| | | | C | H | N |
| 50 | $CH_3CH_2CH_2-$ | $-CH_2-\text{C}_6\text{H}_4-OH$ | 63.31 (64.43 | 7.50 7.46 | 3.01 3.58) |
| 51 | $\text{C}_6\text{H}_5-CH_2CH_2-$ | $-CH_2-\text{(indole-3-yl)}$ | 63.00 (63.14 | 6.28 6.87 | 7.18 8.18) |
| 52 | $\text{C}_6\text{H}_5-CH_2CH_2-$ | $-CH_2-\text{C}_6\text{H}_5$ | 68.42 (68.47 | 7.06 6.90 | 6.05 6.39) |

| Example No. | R²Y | R³ | R⁴ | Analysis % (Theoretical in brackets) | | |
|---|---|---|---|---|---|---|
| | | | | C | H | N |
| 53 | $CH_3CH_2CH_2-$ | $-CH_2-\text{C}_6\text{H}_4-OCH_2CH_3$ | H | 65.62 (65.84 | 8.06 7.93 | 3.03 3.34) |
| 54 | $CH_3CH_2CH_2-$ | $-CH_2-\text{C}_6\text{H}_4-OCH(CH_3)_2$ | H | 65.28 (65.14 (0.5 mole $H_2O$) | 8.13 8.20 | 3.02 3.16) |
| 55 | $CH_3CH_2CH_2-$ | $-CH_2-\text{C}_6\text{H}_3(Cl)-OH$ (R,S) | H | 60.07 (59.66 (0.5 mole $H_2O$) | 7.15 7.18 | 2.98 3.02) |

EXAMPLE 56

N-[1-(3-Aminopropyl-2-(S)-t-butyloxycarbonyl)-1-cyclopentane-carbonyl-O-t-butyl-(S)-tyrosine t-butyl ester N-[1-(2-t-Butyloxycarbonyl-3-dibenzylaminopropyl)-1-cyclopentanecarbonyl]-O-t-butyl-(S)-tyrosine t-butyl ester (from Example 1, 19 g) was dissolved in an ethanol:water mixture (8:1, 300 ml) and hydrogenated under an atmosphere of hydrogen (60 p.s.i., 4.1 bar) at room temperature, over 20% palladium hydroxide on carbon (2 g). After 24 hours, the solution was filtered through a solkafloc pad, and the filtrate evaporated to yield an oil which crystallised. This was triturated with hexane, chilled and filtered to yield the pure enantiomer title compound as a solid (6 g, 42%) m.p. 122°–127° C. Found: C,67.90: H,9.33; N,5.08. $C_{31}H_{50}N_2O_6$ requires C,68.09; H,9.22; N,5.12%.

EXAMPLES 57-78

The following compounds were prepared from the corresponding dibenzylaminopropyl starting material following the procedure of Example 56.

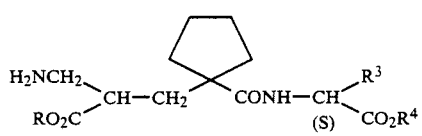

| Example No. | R | R³ | R⁴ | Analysis % (Theoretical in brackets) | | |
|---|---|---|---|---|---|---|
| | | | | C | H | N |
| 57 | $(CH_3)_3C-$ | $-CH_2-\text{C}_6\text{H}_4-OH$ | $(CH_3)_3C-$ | 64.40 (66.09 | 8.74 8.63 | 5.48 5.71 |

-continued

| Example No. | R | R³ | R⁴ | Analysis % (Theoretical in brackets) | | |
|---|---|---|---|---|---|---|
| | | | | C | H | N |
| 58 | (CH₃)₃C— | —CH₂—C₆H₄—OC(CH₃)₃ | C₂H₅— | 66.57 (66.37) | 8.88 (9.15) | 5.14 (5.53) |
| 59 | (CH₃)₃C— | —CH₂—C₆H₅ | (CH₃)₃C— | 68.27 (68.32) | 9.10 8.92 | 6.06 5.90 |
| 60 | (CH₃)₃C— | —CH₂—C₆H₄—NHSO₂CH₃ | C₂H₅— | 59.72 (59.84) | 7.32 7.17 | 8.13 8.31 |
| 61 | (CH₃)₃C— | —CH₂—C₆H₄—OCH₃ | C₂H₅— | 65.78 (65.52) | 8.53 8.46 | 5.58 5.88 |
| 62 | (CH₃)₃C— | —CH₂—C₆H₄—NHSO₂CH₃ | CH₃CH₂— | 56.62 (56.91) (0.5 mole H₂O) | 7.62 7.71 | 7.73 7.65 |
| 63 | (CH₃)₃C— | —CH₂—C₆H₄—OC(CH₃)₃ | 3-pentyl | 67.69 (67.72) (0.1 mole CH₂Cl₂) | 9.33 9.21 | 4.89 4.92 |
| 64 | (CH₃)₃C— | —CH₂—C₆H₄—OC(CH₃)₃ | cyclohexyl | Rf 0.33 (CH₂Cl₂, CH₃OH, NH₄OH; 90:10:1) | | |
| 65 | (CH₃)₃C— | —CH₂—C₆H₄—OC(CH₃)₃ | 2,4-dimethyl-pentyl | Rf 0.58 (CH₂Cl₂, CH₃OH, NH₄OH; 90:10:1) | | |
| 66 | (CH₃)₃C— | —CH₂—C₆H₄—OC(CH₃)₃ | 3-phenpropyl | 68.12 (68.13) (0.3 mole CH₂Cl₂) | 8.26 8.44 | 4.45 4.30 |
| 67 | (CH₃)₃C— | —CH₂—C₆H₄—OC(CH₃)₃ | 4-t-butyl-cyclohexyl | 69.81 (70.66) | 9.45 9.62 | 4.29 4.45 |
| 68 | (CH₃)₃C— | —CH₂—C₆H₄—OH | 2,4,6-tri-methylphenyl | 68.63 (68.50) (0.125 mole CH₂Cl₂) | 8.89 7.92 | 5.17 4.97 |
| 69 | CH₃CH₂— | —CH₂—C₆H₄—OC(CH₃)₃ | (CH₃)₃C— | 67.46 (67.15) | 8.84 8.94 | 5.35 5.40 |

-continued

| Example No. | R | R³ | R⁴ | Analysis % (Theoretical in brackets) C H N |
|---|---|---|---|---|
| 70 | $C_6H_5(CH_2)_3-$ | $-CH_2-\text{C}_6\text{H}_4-OC(CH_3)_3$ | $(CH_3)_3C-$ | (gum) |
| 71 | $CH_3CH_2-$ | $-CH_2-\text{C}_6\text{H}_4-OH$ | $CH_3CH_2-$ | Rf 0.71 (CH₂CH₂, CH₃OH, AcOH; 90:10:1) |
| 72 | $(CH_3)_3C-$ | $-CH_2-\text{C}_6\text{H}_4-OH$ | $CH_3CH_2-$ | 65.15  8.29  6.22 (64.91  8.28  6.06) |
| 73 | $(CH_3)_3C-$ | $-CH_2-\text{C}_6\text{H}_4-OH$ | cyclohexyl | 66.74  8.64  5.33 (66.74  8.61  5.36) (0.29 mole H₂O) |
| 74 | $(CH_3)_3C-$ | $-CH_2-\text{C}_6\text{H}_4-OH$ | cycloheptyl | 66.86  8.53  4.98 (66.75  8.40  5.19) |
| 75 | $(CH_3)_3Si(CH_2)_2-$ | $-CH_2-\text{C}_6\text{H}_4-OC(CH_3)_3$ | $(CH_3)_3-$ | 64.58  9.21  4.70 (65.04  9.21  4.74) |
| 76 | $(CH_3)_3Si(CH_2)_2-$ (S-isomer) | $-CH_2-\text{C}_6\text{H}_4-OC(CH_3)_3$ | $(CH_3)_3C-$ | 65.02  9.28  4.78 (65.04  9.21  4.74) |
| 77 | $(CH_3)_3Si(CH_2)_2-$ | $-CH_2-\text{C}_6\text{H}_4-NHSO_2CH_3$ | $(CH_3)_3C-$ | 56.76  8.09  7.11 (56.92  8.07  6.89) |
| 78 | $(CH_3)_3C-$ (S-isomer) | $-CH_2-\text{C}_6\text{H}_4-OC(CH_3)_3$ | $CH_3CH_2-$ | 66.19  8.69  5.22 (66.29  8.83  5.31) (0.1 mole CH₂Cl₂) |

EXAMPLE 79

N-[1-(2-(S)-t-Butyloxycarbonyl-3-N-methylaminopropyl)-1-cyclo-pentane-carbonyl]-O-t-butyl-(S)-tyrosine t-butyl ester (a) A stirred solution of N-[1-(3-aminopropyl-2-(S)-t-butyloxy-carbonyl)-1-cyclopentanecarbonyl]-O-t-butyl-(S)-tyrosine t-butyl ester (2.0 g, 1 equiv) and N-methylmorpholine (0.55 g, 1.5 equiv) in dry dichloromethane (17 ml) was cooled in ice and trifluoroacetic anhydride (1.0 g, 1.3 equiv) in dichloromethane (3 ml) added dropwise over 20 minutes. The solution was stirred for 30 minutes at which time a further aliquot of trifluoroacetic anhydride (0.5 g) was added and the solution stirred for a further 30 minutes. The reaction mixture was diluted with diethyl ether (10 ml), washed with water (2×10 ml), dilute hydrochloric acid (2×10 ml), dried (MgSO₄) filtered and the solvent evaporated to yield N-[1-(2-(S)-t-butyloxycarbonyl-3-trifluoroacetamidopropyl)-1-cyclopentane-carbonyl]-O-t-butyl-(S)-tyrosine t-butyl ester as a yellow gum (2.2 g, 94%)

(b) Dry potassium carbonate (1 g, 2.0 equiv) was added to a cooled and stirred solution of the above product (2.2 g, 1.0 equiv) and methyl iodide (2.0 g; 0.9 ml, 4.0 equiv) in dry dimethylformamide (10 ml) and the mixture allowed to warm to room temperature and stirred overnight. The reaction mixture was diluted with ethyl acetate (20 ml) and washed with water (10 ml), dilute hydrochloric acid (5×5 ml), dried (MgSO₄), filtered and the solvent evaporated to yield the 3-N-methyltrifluroacetamide derivative as a yellow gum (1.95 g, 87%).

(c) Sodium hydroxide (0.14 g, 1.2 equiv) was added to an ice-cooled and stirred solution of the above trifluoracetamide (1.94 g, 1.0 equiv) in ethanol (10 ml), and the reaction allowed to war(R)to room temperature for an hour. The reaction mixture was concentrated by evaporation under reduced pressure and diluted with a mixture of ethyl acetate (20 ml) and water (5 ml). The organic phase was separated and the aqueous phase re-extracted with ethyl acetate (10 ml). The combined organic extracts were dried (MgSO₄), filtered and the solvent evaporated to yield an oil which crystallised on standing. Recrystallisation from hexane gave the title product (1.24 g, 75%), m.p. 105°–109° C. Found: C, 68.85; H,9.41; N,4.90. C requires $C_{32}H_{52}N_2O_6$ C, 68.54; H,9.35; N,4.99%.

EXAMPLE 80

N-{1-[3-Carboxy-2(R,S)-t-butyloxycarbonylpropyl]-1-cyclopentane-carbonyl}-O-t-butyl-(S)-tyrosine ethyl ester (a) solution of 1-[3-benzyloxycarbonyl-2-t-butyloxycarbonylpropyl]-1-cyclopentanecarboxylic acid (2.55 g, 6.53 mmole) in dry dichloromethane (40 ml) cooled to 0.C, was treated with 1-hydroxybenztriazole (0.97 g, 7.18 mmole); N-methylmorpholine (0.86 g, 8.32 mmole), and 1-ethyl-3-(dimethylaminopropyl)carbodiimide (1.63 g, 8.32 mmole), and the mixture stirred at 0° C. for 10 minutes. O-t-Butyl-(S)-tyrosine-ethyl ester (1.73 g, 6.53 mmole) was added, and the reaction allowed to warm to room temperature and stirred overnight. The solvent was then removed from the reaction under reduced pressure and the resultant gum allowed to stand for a further 48 hours at room temperature. The reaction mixture was then partitioned between ethyl acetate (100 ml) and water (50 ml). The organic phase was separated and then washed with water (2×30 ml), saturated brine (30 ml), dried (MgSO₄), filtered, and the solvent evaporated to yield the crude product as an oil. Chromatography over silica gel, eluting with mixtures of hexane and diethyl ether gave N-{1-[3-benzyloxycarbonyl-2(R,S)-t-butyloxycarbonylpropyl]-1-cyclopentane}carbonyl-O-t-butyl-(S)-tyrosine ethyl ester as a yellow oil (2.56 g, 60%). Found: C,69.31; H,8.49; N,2.49. $C_{37}H_{51}NO_8$ requires C,69.67; H,8.06; N,2.20%.

(b) The above product (2.48 g, 3.89 mmole) was dissolved in an ethanol;water mixture (9:1,66 ml) and hydrogenated at room temperature under an atmosphere of hydrogen (60 p.s.i., 4.1 bar) over 10% palladium on carbon (250 mg) for 5 hours. The reaction mixture was filtered through a solkaflok pad, and the filtrate evaporated to dryness. The residue was azeotroped with dichloromethane (3x) to yield the crude product as white foam. Charomatography over silica gel, eluting with mixtures of hexane and ethyl acetate gave the title compound as a white foam (1.83 g, 86%). Found: C,65.48; H,8.33; N,1.92. $C_{20}H_{45}NO_8$ requires C,65.79; H,8.28; N, 2.56%.

EXAMPLE 81

N-{1-[3-(N²,N⁶-Dibenzyloxycarbonyl-(S)-lysylamino)-2(S)-t-butyloxycarbonylpropyl]-1-cyclopentanecarbonyl}-O-t-butyl-(S)-tyrosine-t-butyl ester A solution of N-[1-(3-aminopropyl-2(S)-t-butyloxycarbonyl)-1-cyclopentanecarbonyl]-O-t-butyl-(S)-tyrosine-t-butyl ester (from Example 56, 0.4 g, 0.73 mmole) in dry dichloromethane (10 ml) cooled to 0° C., was treated with 1-hydroxybenztriazole (0.13 g, 0.88 mmole), and 1-ethyl-3-(dimethylaminopropyl)-carbodiimide (0.21 g, 0.88 mmole), and the mixture stirred at 0° C. for 30 minutes. N²,N⁶-Dibenzyloxycarbonyl-(S)-lysine (0.33 g, 0.80 mmole) was added, and the reaction allowed to warm to room temperature and stirred overnight. The reaction mixture was diluted with methylene chloride (5 ml) and washed with water. (2×10 ml), dilute hydrochloric acid (1M, 2×10 ml), aqueous sodium bicarbonate (10 ml) and brine (10 ml), dried (MgSO₄), filtered and the solvent evaporated to yield the crude product as an oil. Chromatography over silica gel, eluting with mixtures of hexane and ethyl acetate gave the title compound as a foam (0.55 g, 85%). Found: C,67.47; H,7.99; N,5.74. C requires C,67.49; H,7.91; N,5.94%.

EXAMPLES 82–144

The following compounds were prepared following the procedure of Example 81 using the appropriate amine of Examples 56 to 79 and coupling with the appropriate amino acid. Z indicates the benzyloxycarbonyl N-protecting group and BOC indicates the t-butyloxycarbonyl group. Unless otherwise indicated $R^2$ and $R^3$ are derived from the naturally occurring amino acids having S stereochemistry.

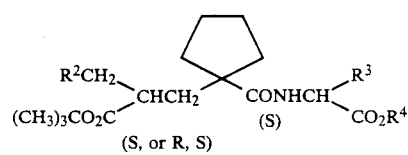

Examples 85–91, 107, 108, 118–141 and 143 are derived from the appropriate amine of formula (VI) from Examples 76–78 having S stereochemistry.

| Example No. | $R^2$ | $R^3$ | $R^4$ | Analysis % (Theoretical in Brackets) | | |
|---|---|---|---|---|---|---|
| | | | | C | H | N |
| 82 | NHCOCH₃<br>\|<br>ZNH(CH₂)₄CH—CONH— | —CH₂—⟨phenyl⟩—OH | (CH₃)₃C— | 64.07<br>(64.96 | 7.90<br>7.86 | 6.76<br>7.04) |
| 83 | NHCO—⟨cyclopentyl⟩<br>\|<br>ZNH(CH₂)₄CHCONH— | —CH₂—⟨phenyl⟩—OH | (CH₃)₃C— | 65.53<br>(66.16 | 7.96<br>7.96 | 6.47<br>6.71) |

-continued

| Example No. | R² | R³ | R⁴ | Analysis % (Theoretical in Brackets) | | |
|---|---|---|---|---|---|---|
| | | | | C | H | N |
| 84 | ZNH(CH₂)₄CH(NHCO-furan)CONH— | —CH₂—C₆H₄—OH | (CH₃)₃C— | 64.10 (65.22 | 7.32 7.38 | 6.39 6.61) |
| 85 | ZNH(CH₂)₄CH(NHSO₂CH₃)CONH— | —CH₂—C₆H₄—OC(CH₃)₃ | (CH₃)₃C— | 62.06 (62.27 | 7.95 7.95 | 6.36 6.31) |
| 86 | ZNH(CH₂)₄CH(OH)CONH— | —CH₂—C₆H₄—OC(CH₃)₃ | (CH₃)₃C— | Rf. 0.66 (silica, ethyl acetate) | | |
| 87 | ZNH(CH₂)₄CH(NHCO-pyridyl)CONH— | —CH₂—C₆H₄—OC(CH₃)₃ | (CH₃)₃C— | 66.60 (67.00 | 7.77 7.83 | 7.57 7.66) |
| 88 | 1-NHZ-cyclopentyl-CONH— | —CH₂—C₆H₄—OC(CH₃)₃ | (CH₃)₃C— | 66.99 (68.24 | 8.11 8.27 | 5.83 5.31) |
| 89 | C₆H₅—CH(NHZ)—CONH— | —CH₂—C₆H₄—OC(CH₃)₃ | (CH₃)₃C— | Rf. 0.9 (silica, ethyl acetate) | | |
| 90 | HO—C₆H₄—CH(NHCO₂C(CH₃)₃)—CONH— | —CH₂—C₆H₄—OC(CH₃)₃ | (CH₃)₃C— | 65.85 (66.38 | 8.38 8.23 | 5.11 5.28) |
| 91 | (CH₃)₃CO₂CNHCH(CONHCH₂C₆H₅)CH₂SO₂NH— (S) | —CH₂—C₆H₄—OC(CH₃)₃ | (CH₃)₃C— | 62.39 (62.27 | 8.09 7.95 | 6.26 6.31) |
| 92 | ZNH(CH₂)₄CH(NHCOCH₃)CONH— | —CH₂—C₆H₄—OC(CH₃)₃ | C₂H₅— | 64.71 (64.31 | 8.08 8.86 | 6.58 7.46) |
| 93 | ZNH(CH₂)₄CH(NHCO-cyclobutyl)CONH— | —CH₂—C₆H₄—OC(CH₃)₃ | C₂H₅— | 67.74 (68.00 | 8.05 8.33 | 6.27 6.61) |
| 94 | ZNH(CH₂)₄CH(NHZ)CONH— | —CH₂—C₆H₄—OC(CH₃)₃ | C₂H₅— | Rf 0.28 and 0.38 (silica, ethylacetate toluene, 1:1) | | |
| 95 | ZNH(CH₂)₄CH(NHSO₂CH₃)CONH— | —CH₂—C₆H₄—OC(CH₃)₃ | C₂H₅— | Rf 0.20 and 0.13 (silica, ethylacetate toluene, 1:1) | | |
| 96 | ZNH(CH₂)₄CH(NHCOCH₃)CONH— | —CH₂—C₆H₅ | (CH₃)₃C— | 66.03 (66.29 | 8.17 8.02 | 6.97 7.19) |

-continued

| Example No. | R² | R³ | R⁴ | Analysis % (Theoretical in Brackets) | | |
|---|---|---|---|---|---|---|
| | | | | C | H | N |
| 97 | ZNH(CH₂)₄CHCONH—, NHCO—cyclobutyl | —CH₂—C₆H₅ | (CH₃)₃C— | 67.19 (67.45 | 8.08 8.12 | 6.78 6.84) |
| 98 | ZNH(CH₂)₄CHCONH—, NHZ | —CH₂—C₆H₄(NHSO₂CH₃) (R,S) | C₂H₅— | 59.46 (59.44 | 6.57 6.58 | 7.63 7.88) |
| 99 | ZNH(CH₂)₄CHCONH—, NHCOCH₃ | —CH₂—C₆H₄(NHSO₂CH₃) (R,S) | C₂H₅— | 59.22 (59.84 | 7.32 7.17 | 8.13 8.31) |
| 100 | ZNH(CH₂)₄CHCONH—, NHSO₂CH₃ | —CH₂—C₆H₄(NHSO₂CH₃) (R,S) | C₂H₅— | 54.64 (54.83 hydrate | 6.89 7.07 | 7.81 7.80) |
| 101 | ZNH(CH₂)₄CHCONH—, NHZ | —CH₂—C₆H₄—OCH₃ | C₂H₅— | 66.07 (66.04 | 7.44 7.39 | 6.43 6.42) |
| 102 | ZNH(CH₂)₄CHCONH—, NHCOCH₃ | —CH₂—C₆H₄—OCH₃ | C₂H₅— | 63.86 (64.60 | 7.79 7.74 | 7.16 7.17) |
| 103 | ZNH(CH₂)₄CHCONH—, NHSO₂CH₃ | —CH₂—C₆H₄—OCH₃ | C₂H₅— | 59.61 (59.61 | 7.38 7.36 | 6.83 6.78) |
| 104 | ZNH(CH₂)₄CHCONH—, OH | —CH₂—C₆H₄—OCH₃ | C₂H₅— | 64.91 (63.23 | 7.46 7.22 | 5.78 6.15) |
| 105 | ZNH(CH₂)₄CHCONH—, NHCO—furyl | —CH₂—C₆H₄—OCH₃ | C₂H₅— | 63.95 (64.10 0.5 mole H₂O | 7.27 7.30 | 6.63 6.65) |
| 106 | ZNH(CH₂)₄CHCONH—, NHCO—cyclobutyl | —CH₂—C₆H₄—OCH₃ | C₂H₅— | 65.11 (65.19 0.5 mole H₂O | 7.92 7.78 | 7.03 6.76)[1] |
| 107 | CH₃SCH₂CH₂CHCONH—, NHCO₂(CH₃)₃ | —CH₂—C₆H₄—OC(CH₃)₃ | (CH₃)₃C— | 62.50 (63.29 | 8.73 8.68 | 5.14 5.40) |
| 108 | ZNH(CH₂)₄CHCONH—, NHSO₂C₆H₅ | —CH₂—C₆H₄—OC(CH₃)₃ | (CH₃)₃C— | 63.99 (64.53 | 7.77 7.65 | 5.47 5.90) |

-continued

| Example No. | R² | R³ | R⁴ | Analysis % (Theoretical in Brackets) C | H | N |
|---|---|---|---|---|---|---|
| 109 | ZNH(CH₂)₄CHCONH— with NHSO₂CH₃ | —CH₂—C₆H₄—OC(CH₃)₃ | 3-pentyl | 62.15 (62.64 | 8.37 8.05 | 6.01 6.22) |
| 110 | ZNH(CH₂)₄CHCONH— with NHSO₂CH₃ | —CH₂—C₆H₄—OC(CH₃)₃ | cyclohexyl | 62.91 (63.13 | 8.04 7.95 | 5.80 6.13) |
| 111 | ZNH(CH₂)₄CHCONH— with NHSO₂CH₃ | —CH₂—C₆H₄—OC(CH₃)₃ | 2,4-dimethyl-pentyl | 63.16 (63.21 (0.125 mole CH₂Cl₂) | 8.32 8.27 | 5.97 5.90) |
| 112 | ZNH(CH₂)₄CHCONH— with NHSO₂CH₃ | —CH₂—C₆H₄—OC(CH₃)₃ | 3-phenpropyl | 63.27 (63.21 (0.3 mole CH₂Cl₂) | 7.72 7.51 | 5.57 5.74) |
| 113 | ZNH(CH₂)₄CHCONH— with NHSO₂CH₃ | —CH₂—C₆H₄—OC(CH₃)₃ | 4-t-butyl-cyclohexyl | 64.29 (64.43 | 8.37 8.32 | 5.62 5.78) |
| 114 | ZNH(CH₂)₄CHCONH— with NHSO₂CH₃ | —CH₂—C₆H₄—OH | 2,4,6-tri-methylphenyl | 61.75 (61.52 | 7.20 7.07 | 5.96 6.06) |
| 115 | BOCNH(CH₂)₄CHCONH— with NHSO₂CH₃ | —CH₂—C₆H₄—OH | CH₃CH₂— | 57.34 (57.79 | 7.89 7.86 | 6.98 7.29) |
| 116 | BOCNH(CH₂)₄CHCONH— with NHSO₂CH₃ | —CH₂—C₆H₄—OH | cyclohexyl | 59.45 (59.83 | 8.11 8.08 | 6.54 6.81) |
| 117 | ZNH(CH₂)₄CHCONH— with NHSO₂CH₃ | —CH₂—C₆H₄—OH | cyclo-heptyl | 62.32 (62.12 | 7.65 7.53 | 6.29 6.44) |
| 118 | BOCNH(CH₂)₄CHCONH— with NHZ | —CH₂—C₆H₄—OC(CH₃)₃ | (CH₃)₃C— | 65.32 (66.05 | 8.45 8.42 | 5.87 6.16) |
| 119 | ZNH(CH₂)₄CHCONH— with NHSO₂CH₂C₆H₅ | —CH₂—C₆H₄—OC(CH₃)₃ | (CH₃)₃C— | 64.44 (64.84 | 7.81 7.74 | 5.74 5.82) |
| 120 | ZNH(CH₂)₄CHCONH— with NHSO₂(CH₂)₂CH₃ | —CH₂—C₆H₄—OC(CH₃)₃ | (CH₃)₃C— | 60.51 (60.82 | 7.83 7.89 | 5.87 5.85) |

-continued

| Example No. | R² | R³ | R⁴ | Analysis % (Theoretical in Brackets) C | H | N |
|---|---|---|---|---|---|---|
| 121 | ZNH(CH₂)₄CHCONH— with NHSO₂-C₆H₄-Cl substituent | —CH₂—C₆H₄—OC(CH₃)₃ | (CH₃)₃C— | 61.74 (62.27 | 7.37 7.27 | 5.33 5.70) |
| 122 | BOCNH— cyclopentane —NCOC₆H₅, CONH— | —CH₂—C₆H₄—OC(CH₃)₃ | (CH₃)₃C— | 66.89 (66.80 | 8.36 8.17 | 6.64 6.49) |
| 123 | ZNH(CH₂)₄CHCONH— with NHCH₂C₆H₅ | —CH₂—C₆H₄—OC(CH₃)₃ | (CH₃)₃C— | Rf 0.82 (Ethyl acetate) | | |
| 124 | BOCNH(CH₂)₄CHCONH— with CH₃ (S) | —CH₂—C₆H₄—OC(CH₃)₃ | (CH₃)₃C— | Gum, Rf 0.36 (ethyl acetate, toluene; 1:1) | | |
| 125 | BOCNZ(CH₂)₄CHCONH— with CH₂C₆C₅ (R) | —CH₂—C₆H₄—OC(CH₃)₃ | (CH₃)₃C— | Gum, Rf 0.62 (ethyl acetate, toluene; 1:1) | | |
| 126 | BOCNZ(CH₂)₄CHCONH— with CH₂OCH₂C₆H₅ (R) | —CH₂—C₆H₄—OC(CH₃)₃ | (CH₃)₃C— | Gum, Rf 0.7 (ethyl acetate, toluene; 1:1) | | |
| 127 | ZNH(CH₂)₅CONH— (R,S) | —CH₂—C₆H₄—OC(CH₃)₃ | (CH₃)₃C— | Gum, Rf 0.9 (ethyl acetate) | | |
| 128 | CH₃S(CH₂)CHCONH— with NHCH₂C₆H₅ | —CH₂—C₆H₄—OC(CH₃)₃ | (CH₃)₃C— | Gum, Rf 0.41 (ethyl acetate, toluene; 1:1) | | |
| 129 | BOCNH(CH₂)₄CHCONH— with CH₂CH=CH—C₆H₅ | —CH₂—C₆H₄—OC(CH₃)₃ | (CH₃)₃C— | Gum Rf 0.71 (ethyl acetate, toluene; 1:1) | | |
| 130 | CH₃(CH₂)₃CHCONH— with NHBOC (S) | —CH₂—C₆H₄—OC(CH₃)₃ | (CH₃)₃C— | 66.47 (66.37 | 9.33 9.15 | 5.23 5.53) |
| 131 | C₆H₅CH₂OCH₂CHCONH— with NHBOC (S) | —CH₂—C₆H₄—OC(CH₃)₃ | (CH₃)₃C— | 66.85 (66.50 0.1 mole CH₂Cl₂ | 8.56 8.34 | 5.06 5.05) |
| 132 | C₆H₅CH₂OCH—CHCONH— with CH₃ (R), NHBOC (S) | —CH₂—C₆H₄—OC(CH₃)₃ | (CH₃)₃C— | 67.27 (67.35 | 8.66 8.54 | 5.01 5.01) |

-continued

| Example No. | R² | R³ | R⁴ | Analysis % (Theoretical in Brackets) | | |
|---|---|---|---|---|---|---|
| | | | | C | H | N |
| 133 | BOC-N(imidazole)-CH₂-CH(NHBOC)-CONH— (S) | —CH₂—C₆H₄—OC(CH₃)₃ | (CH₃)₃C— | 63.27 (63.07 | 8.34 8.36 | 7.87 7.82) (0.6 mole H₂O) |
| 134 | C₆H₅CH₂OCH₂-CH(NHBOC)-CONH— (R) | —CH₂—C₆H₄—OC(CH₃)₃ | (CH₃)₃C— | 61.81 (62.10 | 7.58 7.87 | 4.45 4.62) (1 mole CH₂Cl₂) |
| 135 | (imidazole-NH)-CH₂-CH(NHCOCH₃)-CONH— (S) | —CH₂—C₆H₄—OC(CH₃)₃ | (CH₃)₃C— | Rf 0.52 (CH₂Cl₂, CH₃OH, AcOH, 80:20:1) | | |
| 136 | (imidazole)N—CH₂CH(NHCOCH₃)CONH— (R,S) | —CH₂—C₆H₄—OC(CH₃)₃ | (CH₃)₃C— | 62.60 (62.66 | 8.07 8.28 | 8.91 9.37) (1.3 mole H₂O) |
| 137 | HO—C₆H₄—CH(NHBOC)—CONH— (R) | —CH₂—C₆H₄—OC(CH₃)₃ | (CH₃)₃C— | 65.08 (64.92 | 8.33 8.30 | 5.01 5.16) (hydrate) |
| 138 | C₆H₅CH₂OCH₂CH(NHBOC)CH₂CONH— (R) | —CH₂—C₆H₄—OC(CH₃)₃ | (CH₃)₃C— | 67.04 (67.36 | 8.64 8.54 | 5.09 5.01) |
| 139 | (N-Z-pyrrolidin-2-yl)-CH₂CONH— (S) | —CH₂—C₆H₄—OC(CH₃)₃ | (CH₃)₃C— | 67.61 (67.47 | 8.30 8.30 | 5.49 5.25) (hemi-hydrate) |
| 140 | BOCNHCH₂CH(NHZ)CONH— (S) | —CH₂—C₆H₄—OC(CH₃)₃ | (CH₃)₃C— | 64.44 (64.43 | 8.19 8.17 | 6.43 6.40) (hemi-hydrate) |
| 141 | BOCNHCH₂CH(NHCOC₆H₅)CONH— (S) | —CH₂—C₆H₄—OC(CH₃)₃ | (CH₃)₃C— | 65.67 (66.00 | 7.98 8.19 | 6.39 6.69) |
| 142 | (CH₃)₂CHCH₂CH(NHZ)CONH— (S) | —CH₂—C₆H₄—OH | (CH₃)₃C— | 66.96 (68.07 | 8.60 8.51 | 5.38 5.29) |
| 143 | BOCNH(CH₂)₄CH(NHSO₂CH₃)CONH— (S) (S) | —CH₂—C₆H₄—OC(CH₃)₃ | CH₃CH₂— | 58.76 (58.76 | 8.16 8.35 | 6.04 6.69) (0.7 mole H₂O) |
| 144 | BOCNH(CH₂)₄CH(NHSO₂CH₃)CONH— (S) (R,S) | —CH₂—C₆H₄—OC(CH₃)₃ | CH₃CH₂— | 59.31 (59.69 | 8.20 8.31 | 7.08 6.79) |

EXAMPLES 145-150

The following compounds were prepared according to the method of Example 81 using the appropriate amine.

EXAMPLES 151-152

The following compounds were prepared according to the method of Example 81 starting with the N-methyl amine of Example 79.

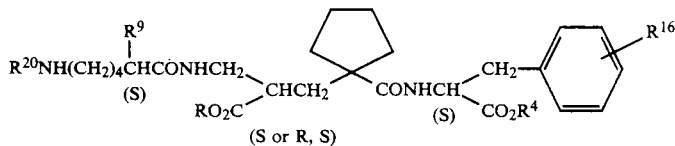

| Example No | R | $R^{20}$ | $R^9$ | $R^{16}$ | $R^4$ | Analysis % (Theoretical in brackets) | | |
|---|---|---|---|---|---|---|---|---|
| | | | | | | C | H | N |
| 145 | $CH_3CH_2-$ | Z | $-NHSO_2CH_3$ | $-OC(CH_3)_3$ | $-C(CH_3)_3$ | 60.30 (60.32 (hydrate) | 7.67 7.71 | 6.69 6.39) |
| 146 | $C_6H_5(CH_2)_3-$ | Z | $-NHSO_2CH_3$ | $-OC(CH_3)_3$ | $-C(CH_3)_3$ | Rf 0.27 (toluene, ethyl acetate 1:1) | | |
| 147 | $CH_3CH_2-$ | Z | $-NHBOC$ | $-OH$ | $-CH_2CH_3$ | 63.02 (63.30 | 7.68 7.59 | 6.80 7.03) |
| 148 | $(CH_3)_3Si(CH_2)_2-$ (S, RS, S) | BOC | $-NHZ$ | $-OC(CH_3)_3$ | $-C(CH_3)_3$ | 64.33 (64.26 | 8.48 8.46 | 5.71 5.88) |
| 149 | $(CH_3)_3Si(CH_2)_2-$ (S, S, S) | BOC | $-NHZ$ | $-OC(CH_3)_3$ | $-C(CH_3)_3$ | 64.30 (64.26 | 8.72 8.46 | 5.99 5.88) |
| 150 | $(CH_3)_3Si(CH_2)_2-$ | BOC | $-NHZ$ | $-NHSO_2CH_3$ | $-C(CH_3)_3$ | gum | | |

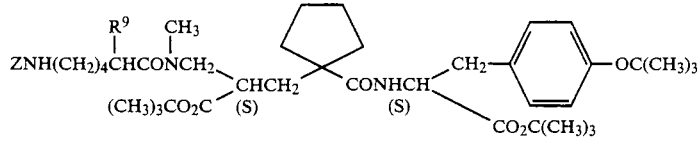

| Example No | $R^9$ | Analysis % (Theoretical in brackets) | | |
|---|---|---|---|---|
| | | C | H | N |
| 151 | $-NHSO_2CH_3$ | Rf 0.86 ($CH_2Cl_2$, $CH_3OH$, $NH_4OH$; 90:10:1) | | |
| 152 | $-NHCO_2CH_2C_6H_5$ | 67.23 (67.75 | 8.20 8.00 | 5.54 5.85) |

Examples 153-156

The following compounds were prepared by the method of Example 81 starting with the acid of Example 80 and coupling with the appropriate amine.

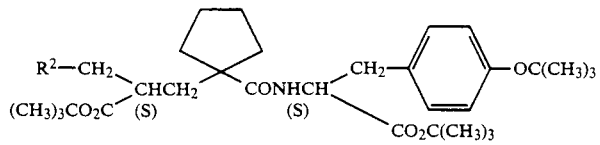

| Example No | $R^2$ | Analysis % (Theoretical in brackets) | | |
|---|---|---|---|---|
| | | C | H | N |
| 153 | $ZNH(CH_2)_4NHCO-$ | 66.55 (67.08 | 8.03 8.18 | 5.60 5.59) |
| 154 | $\begin{array}{c}CH_2C_6H_5\\|\\ZNH(CH_2)_4NCO-\end{array}$ | 69.76 (69.89 | 8.14 8.02 | 4.59 4.99) |

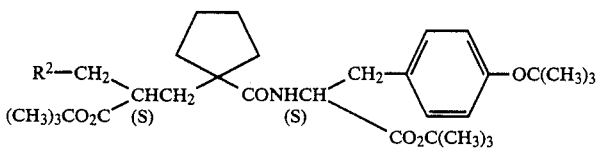

| Example No | R² | Analysis % (Theoretical in brackets) | | |
|---|---|---|---|---|
| | | C | H | N |
| 155 | CH₂OH<br>\|<br>ZNH(CH₂)₄CHNHCO—<br>(S) | Rf 0.48<br>(ethyl acetate) | | |
| 156 | [imidazole]—CH₂CHNHCO—<br>         \|<br>         CH₂OH<br>(S) | 62.86<br>(62.77<br>(hydrate) | 8.09<br>8.19 | 7.87<br>8.13) |

EXAMPLE 157

N-{1-3-(N²-Methanesulphonyl-N⁶-t-butyloxycarbonyl-(S)-lysylino)-2(R,S)-trimethylsilylethoxycarbonyl-propyl]-1-cyclopentane-carbony}-O-t-butyl-(S)-tyrosine-t-butyl ester A solution of N-{1-[3-(N⁶-t-butyloxycarbonyl-(S)-lysylamino-2(R,S)-trimethylsilylethoxycarbonyl propyl]-1-cyclopentane-carbonyl}-O-t-butyl-(S)-tyrosine-t-butyl ester, (2.5 g, 3.1 mmole) in ice-cold dichloromethane (50 ml) was treated with pyridine (1.25 g, 15.8 mmole) and methanesulphonyl chloride (860 mg, 7.5 mmole) and stirred overnight at room temperature. The solvents were removed under reduced pressure and the residue partitioned between between ethyl acetate and dilute citric acid. The combined extracts were washed with dilute aqueous sodium bicarbonate and brine, dried and evaporated to give a yellow foam which was ehromatographed on silica gel eluting with a mixture of hexane, ethyl acetate and methanol (80:20:5) to give the title product as a colourless foam (1.92 g, 69%). Found: C,58.64; H,8.50; N,6.01. C₄₄H₇₆N₄O₁₀.₁₁S Si requires C,58.89; H,8.54; N,6.24%.

EXAMPLE 158

The fully resolved material was prepared in identical fashion to the above Example starting with the S,S,S isomer to give N-{1-[3-(N²-Methanesulphonyl-N⁶-t-butoxycarbonyl-(S)-lysylamino)-2(S)-trimethylsilylethoxycarbonylpropyl]-1-cyclopentanecarbonyl}-O-t-butyl(S)-tyrosine-t-butyl ester. Found C,59.20; H,8.60; N,6.23%.

EXAMPLE 159

N-{1-[3-(N⁶-Benzyloxycarbonyl-N²-methanesulphonyl-(S)-lysylamino)-N-2(R,S)-ethoxycarbonylpropyl]-1-cyclopentanecarbonyl}-(S)-tyrosine ethyl ester The above procedure was followed starting with the corresponding N⁶-benzyloxycarbonyl derivative to give the title product. Found: C,56.61, H,6.80, N,6.67. C₃₈H₅₄N₄O₁₁S (0.75 CH₂Cl₂) requires C,55.50; H,6.67; N,6.88%.

EXAMPLE 160

N-{1-[3-(N⁶-t-Butoxycarbonyl-N²-acetyl-(S)-lysylamino) 2-(2-trimethylsilyl)ethoxycarbonylpropyl]-1-cyclopentanecarbonyl}-3-methanesulphonamido-(S)-phenylalanine t-butyl ester The procedure of Example 157 was followed but using the appropriate diester and reacting with acetyl chloride instead of methanesulphonyl chloride to give the title N²-acetyl derivative as a colourless foam.

EXAMPLE 161

N-{1-[3-(N²-Methanesulphonyl-N⁶-t-butyloxycarbonyl-(S)-lysylamino-2(R,S)-carboxypropyl]-1-cyclopentanecarbonyl}-O-t-butyl-(S)-tyrosine-t-butyl ester A solution of N-{1-[3-(N²-methanesulphony-N⁶-t-butyloxycarbonyl-(S)-lysylamino-2(R,S)-trimethyl-silylethoxycarbonylpropyl]-1-cyclopentanecarbonyl}-O-t-butyl-(S)-tyrosine-t-butyl ester (1.80 g, 2.0 mmole) in tetrahydrofuran (20 ml) was treated with a solution of tetrabutylammonium fluoride in tetrahydrofuran (1M, 3 ml, 3.0 mmole) and heated to 60° C. under nitrogen. The solvent was removed under reduced pressure, the residue partitioned between ethyl acetate and dilute citric acid, the combined extracts washed with brine, dried and the solvent evaporated to give a foam which was chromatographed on silica gel eluting with ethyl acetate, methanol, hexane, (4:1:5) to give the Pure title product as a foam (1.17 g 74%). Found: C,57.49; H,7.89; N,6.93. C₃₉H₆₄N₄O₁₁S. H₂O requires C,57.46; H,8.16, N,6.87%.

EXAMPLE 162

The fully resolved material was prepared in identical fashion to the above from the S,S,S isomer produced in Example 158 to give N-{1-[3-(N²-methanesulphonyl-N⁶-t-butoxycarbonyl-(S)-lysylamino-2(S)-carboxypropyl]-1-cyclopentanecarbonyl}-O-t-butyl-(S)-tyrosine-t-butyl ester. Found:C,59.01; H,8.21; N,6.87. C₃₉H₆₄N₄O₁₁S requires C,58.77; H,8.09; N,7.03%

EXAMPLE 163

N-{1-[3-(N²-Methanesulphonyl-N⁶-t-butyloxycarbonyl-(S)-lysyl-amino)-2(R,S)-t-butyloxycarbonylpropyl]-1-cyclopentanecarbonyl}-O-t-butyl-(S)-tyrosine N-{1-[3-(N²-Methanesulphonyl-N⁶-t-butyloxycarbonyl-(S)-lysyl-amino)-2(R,S)-t-butyloxycarbonylpropyl]-1-cyclopentanecarbonyl}-O-t- butyl-(S)-tyrosine ethyl ester (2.21 g, 2.68 mmol) was dissolved in acetone (5.5 ml) and then a 1N aqueous solution of sodium hydroxide (5.36 ml, 5.38 mmol) was added. After stirring for 10 minutes at room temeprature the solution was acidified to pH4 with aqueous citric acid (10%). The acetone was then removed on a rotary evaporator and the residue extracted with ethyl acetate (50 ml). The organic phase was separated, washed with saturated brine, dried over magnesium sulphate and the solvent removed under reduced pressure to yield the title compound as a white foam (1.89 g, 88%). Found: C,58.49; H,8.01; N,6.64. $C_{19}H_{64}N_4O_{11}S$ requires C,58.77; H,8.09; N,7.03%.

EXAMPLE 164

N-{1-[3-N²-Methanesulphony-N⁶-t-butyloxycarbonyl-(S)-lysylamino-b 2-(S)-t-butyloxycarbonylpropyl]-1-cyclopentanecarbonyl}-O-t-butyl-(S)-tyrosine The procedure of Example 163 was followed using the resolved starting material of Example 143 to yield the title compound. Found: C,58.17; H,8.09; N,6.42. $C_{39}H_{64}N_4O_{11}S$ (0.66 $H_2O$) requires C,57.89; H,8.14; N,6.93%.

EXAMPLE 165

N-{1-3-(N⁶-Benzyloxycarbonyl-N²-methanesulphonyl-(S)-lysylamino)-2-(S)-carboxypropyl]-1-cyclopentanecarbonyl}-O-benzyl-(S)-tyrosine benzyl ester (a) Aqueous sodium hydroxide (1N, 9.2 ml, 1 eq) was added to a solution of 1-(3-bis(S)-α-methylbenzyl)amino-2-(S)-butoxycarbonylpropyl)-cyclopentane carboxylic acid (4.5 g, 1 eq) in aqueous ethanol (9:1, 80 ml), and the resultant mixture hydrogenated over 20 % palladium hydroxide (0.5 g) at 60 p.s.i. (4.1 bar) and room temperature overnight. A further 0.5 g of catalyst was added and the hydrogenation continued for a further five hours when t.l.c. indicated the reaction was complete. The catalyst was removed by filtration and the reaction mixture evaporated under reduced pressure. The residue was azeotroped twice with dichloromethane and the amine product finally taken up in dichloromethane and used directly in the next reaction.

(b) To an ice cold solution of N²-trichloroethoxycarbonyl-N⁶-benzyloxycarbonyl-(S)-lysine (4.17 g) in dry dichloromethane (20 ml) was added 1-hydroxy-benztriazole (1.49 g), and 1-ethyl-3-(dimethylaminopropyl)-carbodiimide (4.46 g) and the resulting solution stirred at 0° C. for 30 minutes. To this was added a solution of 1-(2-(S)-t-butoxycarbonyl-3-aminopropyl)cyclopentane carboxylic acid sodium salt in dichloromethane (10 ml) from part (a), and the reaction allowed to warm to room temperature and stirred overnight. The reaction was evaporated to dryness and the residue partitioned between ethyl acetate (20 ml) phase washed with water (2×10 ml), 1N hydrochloric acid (2×10 ml), aqueous sodium bicarbonate, brine and then dried (MgSO₄), filtered, and evaporated to yield the crude product as an oil. This was chromatographed over silica gel (160 g) eluting with mixtures of hexane and ethyl acetate. The desired fractions were combined, concentrated then azeotroped with toluene to yield the pure product as a foam (4.28 g, 66%).

(c) The activated ester of this material (4.63 g in dichloromethane (20 ml) was prepared as described in part (b), and treated at 0° C. with a solution of O-benzyl-(S)-tyrosine benzyl ester tosylate salt (3.48 g) and N-methyl-morpholine (1.33 g) in dichloromethane (20 ml). The reaction was allowed to warm to room temperature and stirred overnight. The solution was then evaporated to dryness, the residue dissolved in ethyl acetate and washed with water (2×10 ml), 1N hydrochloric acid (2×10 ml), aqueous sodium bicarbonate, brine, dried (MgSO), filtered and evaporated to yield the crude product as an oil (8.02 g). This was chromatographed over silica gel (130 g), eluting with mixtures of hexane and ethyl acetate. The appropriate fractions were combined and evaporated to yield the pure coupled product as a foam (4.32 g, 68%).

(d) To a cooled solution of the product from part (c) (4.32 g) in acetic acid (25 ml) was added activated zinc dust (4 g) in one portion, and the reaction allowed to warm to a room temperature and stirred. After 90 minutes, the solid residue was removed by filtration, and washed with water. The combined filtrate and washings were evaporated under reduced pressure, and the residue azeotroped with toluene (x3), and then taken up in ethylacetate and washed with aqueous sodium bicarbonate. The organic layer was dried, filtered and evaporated to yield the amine product as a gum.

(e) To a stirred solution of the amine from part (d) (3.38 g), and N-methylmorpholine (0.48 g) in dry dichloromethane (20 ml), cooled to 0° C. was added methanesulphonyl chloride (0.49 g), and the reaction mixture allowed to warm to room temperature and stirred overnight. The reaction mixture was diluted with dichloromethane (20 ml) and washed with water (2×10 ml), 0.1M hydrochloric acid (10 ml), brine and dried (MgSO₄), filtered and evaporated to yield the crude sulphonamide as a foam (4 g). This was chromatographed over silica gel (65 g) eluting with mixtures of hexane and ethyl acetate to give the desired N²-methanesulphonyl product as a foam (2.9 g, 79%).

(f) Trifluoracetic acid (15 ml) was added dropwise to a stirred solution of the product from part (e) (2.87 g), and anisole (0.4 g) in dry dichloromethane (15 ml), cooled to 0° C. After 3 hours, the reaction mixture was evaporated to dryness under reduced pressure. The residue was dissolved in ethyl acetate (30 ml) and washed with aqueous sodium bicarbonate (2×10 ml), 0.1M hydrochloric acid, and brine, dried (MgSO₄), filtered and evaporated to yield the crude product as a yellow oil (3.5 g). This was chromatographed over silica gel (60 g) eluting with mixtures of hexane and ethyl acetate, with 1% acetic acid, to yield the title acid as a foam (2.6 g, 97%). A portion of this material was converted to the caesium salt, using aqueous ethanolic caesium carbonate. Found: C,54.81; H,5.70; N,5.21. $C_{48}H_{57}N_4O_{11}S$ Cs requires C,55.92; H,5.57; N,5.43%.

EXAMPLE 166

N-{1-[3-N⁶-Benzyloxycarbonyl-N²-methanesulphonyl-(S)-lysylamino)-2-(S)-piraloyloxymethoxycarbonylpropyl]-1-cylopentanecarbonyl}-O-benzyl-(S)-tyrosine benzyl ester Pivaloyloxymethlchloride (0.12 g) was added to a stirred solution of the caesium salt from Example 165

(0.55 g) in dry dimethylformamide (6 ml) and the reaction stirred at room temperature overnight. The reaction mixture was diluted with ethyl acetate (20 ml) and washed with water (5×10 ml), 1N hydrochloric acid (2×10 ml), aqueous sodium bicarbonate (10 ml), brine and dried (MgSO$_4$), filtered and evaporated to yield the crude product as a pale yellowish oil (0.7 g). Chromatography over silica gel (12 g) eluting with mixtures of hexane and ethylacetate, gave the title ester as a foam (0.465 g, 88%).

EXAMPLES 167–170

The following products were prepared by the method of Example 166 using the caesium salt of Example 165 and reacting with the appropriate chloride.

ml), dried (MgSO$_4$), filtered and evaporated to yield the crude product as an oil. This was chromatographed over silica gel, eluting with mixtures of ethyl acetate and hexane, to yield the title indanyl ester as a foam (0.93 g, 69%).

EXAMPLE 172

N-{1-[3-(N$^6$-t-Butyloxycarbonyl-N$^2$-methanesulphonyl-(S)-lysylamino)-2(S)-t-butyloxycarbonylpropyl]-1-cyclopentanecarbonyl}-O-t-butyl-(S)-tyrosine-5-indanyl ester The above procedure was followed starting with the acid of Example 164 to give the tyrosine 5-indanyl ester as a foam. Found: C,62.37; H,8.04; N,5.93. C$_{48}$H$_{72}$N$_4$O$_{11}$S requires C,63.13; H,7.95; N,6.14%.

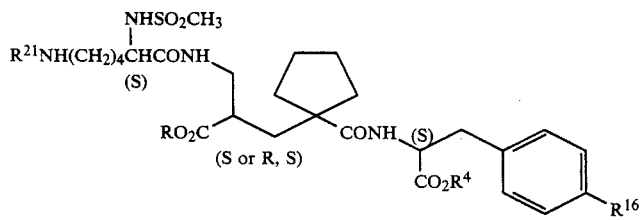

| Example No | R | R$^4$ | R$^{20}$ | R$^{16}$ | Analysis % (Theoretical in brackets) | | |
|---|---|---|---|---|---|---|---|
| | | | | | C | H | N |
| 167 | cyclohexyl-CO$_2$CH(CH$_3$)— (S) | —CH$_2$C$_6$H$_5$ | Z | —OCH$_2$C$_6$H$_5$ | Rf 0.78 | | |
| 168 | C$_2$H$_5$CO$_2$—CH—CH(CH$_3$)$_2$ (S) | —CH$_2$C$_6$H$_5$ | Z | —OCH$_2$C$_6$H$_5$ | Rf 0.86 | | |
| 169 | H$_3$C-dioxolone-CH$_2$— (R,S) | —C(CH$_3$)$_3$ | BOC | —OC(CH$_3$)$_3$ | 58.66 (58.13 | 7.59 7.54 | 5.39 6.16) |
| 170 | (CH$_3$)$_3$C— (R,S) —CH$_2$—cyclohexyl | | BOC | —OC(CH$_3$)$_3$ | 61.65 (61.85 | 8.50 8.58 | 5.94 6.27) |

EXAMPLE 171

N-{1-[3-(N$^6$-Benzyloxycarbonyl-N$^2$-methanesulphonyl-(S)-lysylamino)-2-(S)-indanyloxycarbonylprooyl]-1-cyclopentanecarbonyl}-O-benzyl-(S)-tyrosine benzylester 1-Ethyl-3-(dimethylaminopropyl)-carbodiimide (0.28 g) was added to a solution of the acid from Example 165(f) (1.0 g) and hydroxybenztriazole (0.17 g) in dichloromethane (25 ml) cooled to 0° C. After 10 minutes, N-methyl morpholine (0.42 g), indanol (0.42 g) and dimethylaminopyridine (10 mg) were added, and the mixture stirred for 72 hours. The reaction mixture was diluted with dichloromethane, washed with water (2×10 ml), 2M hydrochloric acid (2×10 ml), brine (10

EXAMPLE 173

N-{1-[3-(N$^2$-Methanesulphonyl-N$^6$-t-butyloxycarbonyl-(S)-lysyl-amino)-2(S)-t-butyloxycarbonylpropyl]-1-cyclopentanecarbonyl}-O-ethoxycarbonyl-(S)-tyrosine-ethyl ester.

Ethyl chloroformate (0.1093 g, 1.007 mmol) was added to an ice-cooled solution of N-{1-[3-(N$^2$-methanesulphonyl-N$^6$-t-butyloxycarbonyl-(S)-lysylamino)-2-(S)-t-butyloxycarbonylpropyl]-1-cyclopentanecarbony}-(S)-tyrosine-ethyl ester (0.7041 g, 0.916 mmol), triethylamine (0.2781 g, 2.75 mmol and 4-dimethylaminopyridine (0.0112 g in dry dichloromethane (20 ml). After 30 minutes the ice-cooling was removed and the reaction stirred overnight at room temperature. The solvent was then evaporated under reduced pressure and the residual oil partitioned between ethyl acetate (50 ml) and 2N hydrochloric acid (50 ml). The phases were separated and the organic phase washed with saturated sodium bicarbonate solution (50 ml), then with saturated brine, (50 ml) and was finally dried over magnesium sulphate, before removing the solvent under reduced pressure to give the crude product as an oil. Chromatography over silica gel, eluting with mixtures of dichloromethane and diethyl ether gave the title compound as a white foam (0.367 g, 48%). Found: C,56.68; H,7.36; N,6.65. $C_{39}H_{64}N_4O_{13}S$ requires C,56.50; H,7.78; N,6.76%.

EXAMPLE 174

N-{1-[3-($N^2$-Methanesulphonyl-$N^6$-t-butyloxycarbonyl-(S)-lysylamino)-2-(R,S)-t-butoxycarbonylpropyl]-1-cyclopentanecarbonyl}-O-cyclohexyloxycarbonyl-(S)-tyrosine-cyclohexyl ester The title compound was prepared in an analogous manner to Example 173 but starting with Example 116 and reacting with cyclohexyl chloroformate to give the title product as a white foam (1.672 g, 81%). Found: C,60.69; H,8.16; N,6.14. $C_{48}H_{76}N_4O_{13}S$ requires C,60.73; H,8.07; N,5.90%.

EXAMPLE 175

N-{1-[2-(S)-t-Butyloxycarbonyl-3($N^6$-t-butyloxycarbonyl-$N^2$-ethyl-(S)-lysylamino)propyl]-1-cyclopentanecarbonyl}-O-t-butyl-(S)-tyrosine-t-butyl ester.

Sodium cyanoborohydride (45 mg) was added in one portion to a stirred, ice cold solution of N-{1-[2-(S)-t-butyloxycarbonyl-3($N^6$-t-butyloxycarbonyl-(S)-lysylamino)propyl]-1-cyclopentanecarbonyl}O-t-butyl-(S)-tyrosine-t-butyl ester (507 mg) and acetaldehyde (31 mg) in aqueous ethanol (80%, 10 ml) and the pH adjusted to 5 with 1N hydrochloric acid. The resulting solution was allowed to warm to room temperature and stirred for 1.5 hours. The reaction mixture was evaporated to dryness and the residue partitioned between water and ethyl acetate. The phases were separated and the organic phase washed with a little aqueous sodium bicarbonate, dried (MgSO$_4$), filtered and evaporated. The residue was chromatographed over silica gel, eluting with mixtures of hexane and ethyl acetate containing 1% diethylamine to yield the title compound as an oil (370 mg, 64%) Rf 0.55 (silica; CH$_2$Cl$_2$, CH$_3$OH, NH$_4$OH; 90:10:1).

EXAMPLE 176

N-{1-[3-($N^2$, $N^6$-Dibenzyloxycarbonyl-(S)-lysylamino)-2(S)-carboxypropyl]-1-cyclopentanecarbonyl}-(S)-tyrosine Hydrogen chloride gas was passed through a stirred, ice cold solution of N-{1-[3-($N^2$,$N^6$-dibenzyloxycarbonyl-(S)-lysylamino)-2-t- butryloxycarbonylpropyl]-1-cyclopentanecarbonyl}-O-t-butyl-(S)- tyrosine-t-butyl ester (from Example 81, 0.445 g, 0.47 mmole), and anisole (0.765 g, 7.1 mmole) in dry dichloromethane (10 ml) until saturation was achieved. A precipitate formed. After stirring for 1.5 hours, the solvent was evaporated under reduced pressure, and the residue azeotroped with dry dichloromethane. The residue was partitioned between ethyl acetate and aqueous sodium bicarbonate. The phases were separated, and the organic phase washed with two further portions of aqueous sodium bicarbonate. The combined aqueous phases were re-extracted with diethyl ether, and then acidified with 1M hydrochloric acid to pH 2. The aqueous phase was extracted with ethyl acetate (2x) and the combined organic phases dried (MgSO$_4$), filtered and the solvent evaporated to yield a foam, which was azeotroped with methylene chloride to yield the title compound as a solid foam (0.325 g, 89%). Found: C,62.81; H,6.68; N,6.92. $C_{41}H_{50}N_4O_{11}$0.4 CH$_2$Cl$_2$ requires C.61.17; H,6.33; N,6.93%.

EXAMPLE 177

N-[1-(2(S)-Carboxy-3-(S)-lysylaminopropyl)-1-cyclopentane carbonyl-(S)-tyrosine

The product from Example 176 (0.247 g, 0.32 mmole) was dissolved in an ethanol:water mixture (9:1, 20 ml) and hydrogenated at room temperature under an atmosphere of hydrogen (60 p.s.i., 4.1 bar) over 10% palladium on carbon (100 mg) overnight. The reaction mixture was filtered through a solkaflok pad, and the filtrate evaporatad to dryness. The residue was azeotroped with dichloromethane (3 x ) to yield the title compound as a foam (0.12 g, 74%). Found: C,56.87; H,7.76; N,10.36. C 0.65 H20 requires C,57.93; H,7.64; N,10.81%.

EXAMPLES 178–213

The following compounds were prepared following the deprotection procedures of Examples 176 and 177 as appropriate starting with the corresponding t-butyl or benzyl ester t-butyloxycarbonyl or benzyloxycarbonyl protected compound. Unless otherwise stated compounds derived from lysine and tyrosine are of (S) stereochemistry.

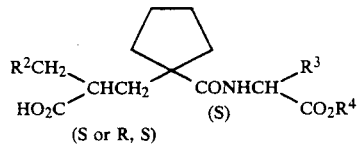

Examples 178–187, 203 and 204 are derived from the resolved compounds having S,S stereochemistry.

| Example No. | $R^2$ | $R^3$ | $R^4$ | Analysis % (Theoretical in Brackets) | | |
|---|---|---|---|---|---|---|
| | | | | C | H | N |
| 178 | NHCOCH$_3$<br>\|<br>H$_2$N(CH$_2$)$_4$CHCONH— | —CH$_2$—⟨phenyl⟩—OH | H | 57.19<br>(58.01<br>(0.5 mole AcOH, 0.125 mole CH$_2$Cl$_2$) | 7.68<br>7.48 | 9.11<br>9.62) |

-continued

| Example No. | R² | R³ | R⁴ | Analysis % (Theoretical in Brackets) | | |
|---|---|---|---|---|---|---|
| | | | | C | H | N |
| 179 | 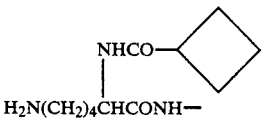 | 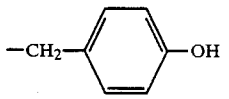 —CH₂—〈 〉—OH | H | 59.38 (61.20 | 7.47 7.53 | 8.97 9.52) |
| 180 | 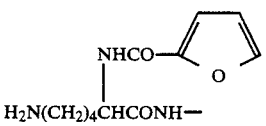 | —CH₂—〈 〉—OH | H | 57.51 (59.98 | 7.09 6.71 | 8.27 9.33) |
| 181 | NHSO₂CH₃<br>H₂N(CH₂)₄CH—CONH— | —CH₂—〈 〉—OH | H | 52.14 (53.16 (0.5 mole EtOH, 0.25 mole H₂O) | 7.35 7.27 | 8.70 8.99) |
| 182 | OH<br>H₂N(CH₂)₄CHCONH— | —CH₂—〈 〉—OH | H | 56.50 (59.15 | 7.48 7.35 | 7.52 8.28) |
| 183 | 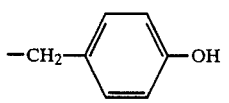 | —CH₂—〈 〉—OH | H | 57.07 (60.86 | 6.82 6.75 | 10.68 11.45) |
| 184 | 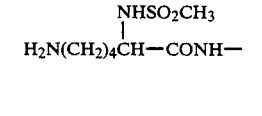 | —CH₂—〈 〉—OH | H | 55.17 (59.58 (1 mole EtOH) | 7.38 7.89 | 5.96 8.02) |
| 185 | 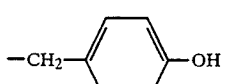 | —CH₂—〈 〉—OH | H | 60.64 (62.67 (0.75 mole AcOH) | 7.02 6.92 | 6.78 7.69) |
| 186 | 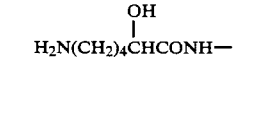 | —CH₂—〈 〉—OH | H | 57.43 (57.79 (HCl, 0.33 mole Et₂O) | 6.47 6.39 | 6.76 7.14) |
| 187 | CONHCH₂C₆H₅<br>H₂NCHCH₂SO₂NH— | —CH₂—〈 〉—OH | H | 52.46 (53.42 (HCl, 0.2 mole Et₂O) | 6.42 6.16 | 7.69 8.36) |
| 188 | NHCOCH₃<br>H₂N(CH₂)₄CHCONH— | —CH₂—〈 〉—OH | C₂H₅— | 57.15 (60.46 | 7.71 7.69 | 6.82 9.72) |
| 189 | 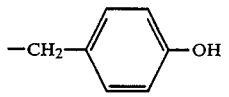 | —CH₂—〈 〉—OH | C₂H₅— | 57.87 (62.32 | 7.49 7.85 | 6.59 7.08) |
| 190 | NH₂<br>H₂N(CH₂)₄CHCONH— | —CH₂—〈 〉—OH | C₂H₅— | 56.82 (60.65 | 7.26 7.29 | 9.05 10.48) |

-continued

| Example No. | R² | R³ | R⁴ | Analysis % (Theoretical in Brackets) C | H | N |
|---|---|---|---|---|---|---|
| 191 | H₂N(CH₂)₄CH(NHSO₂CH₃)CONH— | —CH₂—C₆H₄—OH (para) | C₂H₅— | 53.96 (54.88 | 7.45 7.24 | 8.46 9.14) |
| 192 | H₂N(CH₂)₄CH(NHCOCH₃)CONH— | —CH₂—C₆H₅ | H | 56.84 (59.86 (0.5 mole H₂O) | 7.19 7.63 | 9.25 10.34 |
| 193 | H₂N(CH₂)₄CH(NHCO-cyclobutyl)CONH— | —CH₂—C₆H₅ | H | 58.89 (62.91 | 7.29 7.74 | 8.67 9.78) |
| 194 | H₂N(CH₂)₄CH(NH₂)CONH— | —CH₂—C₆H₄—NHSO₂CH₃ (meta) (R,S) | C₂H₅— | 54.31 (54.17 (0.5 mole H₂O) | 7.71 7.47 | 11.05 11.28) |
| 195 | H₂N(CH₂)₄CH(NHCOCH₃)CONH— | —CH₂—C₆H₄—NHSO₂CH₃ (meta) (R,S) | C₂H₅— | 53.30 (53.00 (1.5 mole H₂O) | 7.55 7.26 | 9.97 10.30) |
| 196 | H₂N(CH₂)₄CH(NHSO₂CH₃)CONH— | —CH₂—C₆H₄—NHSO₂CH₃ (meta) (R,S) | C₂H₅ | 47.95 (47.98 (2.0 mole H₂O) | 6.96 7.08 | 9.05 9.65) |
| 197 | H₂N(CH₂)₄CH(NH₂)CONH— | —CH₂—C₆H₄—OCH₃ | C₂H₅ | 58.99 (59.35 (1.0 mole H₂O) | 8.30 8.18 | 9.23 9.89 |
| 198 | H₂N(CH₂)₄CH(NHCOCH₃)CONH— | —CH₂—C₆H₄—OCH₃ | C₂H₅ | 59.70 (60.08 (0.5 mole H₂O) | 8.02 7.90 | 9.04 9.34 |
| 199 | H₂N(CH₂)₄CH(NHSO₂CH₃)CONH— | —CH₂—C₆H₄—OCH₃ | C₂H₅— | 53.32 (53.27 (0.5 mole H₂O) | 7.41 7.55 | 8.41 8.58) |
| 200 | H₂N(CH₂)₄CH(OH)CONH— | —CH₂—C₆H₄—OCH₃ | C₂H₅— | 59.97 (60.20 (1.5 mole H₂O) | 8.06 7.94 | 7.33 7.52) |
| 201 | H₂N(CH₂)CH(NHCO-2-furyl)CONH— | —CH₂—C₆H₄—OCH₃ | C₂H₅— | 59.57 (59.12 (1.5 mole H₂O) | 7.89 7.37 | 8.10 8.36) |

-continued

| Example No. | R² | R³ | R⁴ | Analysis % (Theoretical in Brackets) C | H | N |
|---|---|---|---|---|---|---|
| 202 | H₂N(CH₂)₄CHCONH— with NHCO-cyclobutyl substituent | —CH₂—C₆H₄—OCH₃ | C₂H₅— | 60.89 (61.09 (1.0 mole H₂O) | 8.04 8.07 | 8.66 8.63 |
| 203 | CH₃SCH₃CH₂CHCONH— with NH₂ | —CH₂—C₆H₄—OH | H | 55.52 (53.71 (1.5 mole H₂O) | 7.16 7.14 | 7.79 7.83) |
| 204 | H₂N(CH₂)₄CHCONH— with NHSO₂C₆H₅ | —CH₂—C₆H₄—OH | H | 55.15 (57.57 | 6.63 6.55 | 8.51 8.66) |
| 205 | H₂N(CH₂)₄CHCONH— with NHSO₂CH₃ | —CH₂—C₆H₄—OH | 3-pentyl | 53.54 (53.54 (2.25 mole H₂O) | 7.60 7.90 | 7.94 8.06) |
| 206 | H₂N(CH₂)₄CHCONH— with NHSO₂CH₃ | —CH₂—C₆H₄—OH | cyclohexyl | 56.85 (57.63 | 8.07 7.56 | 9.35 8.40) |
| 207 | H₂N(CH₂)₄CHCONH— with NHSO₂CH₃ | —CH₂—C₆H₄—OH | 2.4-dimethyl-pentyl | 56.72 (56.72 (0.25 mole CH₂Cl₂) | 8.89 7.80 | 7.61 7.96) |
| 208 | H₂N(CH₂)₄CHCONH— with NHSO₂CH₃ | —CH₂—C₆H₄—OH | 3-phen-propyl | 57.83 (57.83 (1.5 mole H₂O) | 7.08 7.31 | 7.35 7.67) |
| 209 | H₂N(CH₂)₄CHCONH— with NHSO₂CH₃ | —CH₂—C₆H₄—OH | 4-t-butyl-cyclohexyl | 59.25 (59.80 | 8.07 8.08 | 7.80 7.75 |
| 210 | H₂N(CH₂)₄CHCONH— with NHSO₂CH₃ | —CH₂—C₆H₄—OH | 2,4,6-tri-methylphenyl | 5.77 (59.81 | 7.29 7.17 | 7.16 7.97) |
| 211 | H₂N(CH₂)₄CHCONH— with NHSO₂CH₃ | —CH₂—C₆H₄—OH | cycloheptyl | 57.50 (57.54 (0.125 CH₂Cl₂) | 7.76 7.62 | 8.09 8.10) |
| 212 | H₂N(CH₂)₄CHCONH— with NHSO₂CH₃ | —CH₂—C₆H₄—OH | 5-indanyl | 55.10 (54.98 (HCl, 1.5 H₂O, 0.25 dioxan) | 7.08 6.92 | 6.65 7.12) |
| 213 | H₂N(CH₂)₄CHCONH— with NHSO₂CH₃ | —CH₂—C₆H₄—OH | cyclohexyl-methyl | 54.73 (54.78 | 7.65 7.49 | 7.37 7.67) |

EXAMPLES 214–245

The following compounds were prepared from the appropriate t-butyl or benzyl ester/t-butoxycarbonyl or benzyloxycarbonyl protected compound by treatment with HCl and or hydrogenation following the procedure of Examples 176 and 177 as appropriate. Lysine derivatives are of (S) stereochemistry unless otherwise stated.

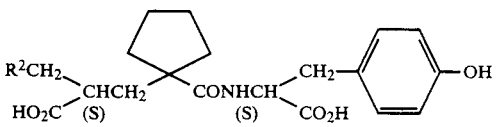

| Example No | $R^2$ | Analysis % (Theoretical in brackets) | | |
|---|---|---|---|---|
| | | C | H | N |
| 214 | H$_2$N(CH$_2$)$_4$CHCONH— <br> \| <br> NHSO$_2$CH$_2$C$_6$H$_5$ | 56.09 <br> (55.15 <br> (2.0 mole H$_2$O) | 6.90 <br> 6.65 | 7.98 <br> 8.04) |
| 215 | H$_2$N(CH$_2$)$_4$CHCONH— <br> \| <br> NHSO$_2$CH$_2$CH$_3$ | 49.98 <br> (50.43 <br> (3.0 mole H$_2$O) | 7.24 <br> 7.55 | 8.13 <br> 8.40) |
| 216 | H$_2$N(CH$_2$)$_4$CHCONH— <br> \| <br> NHSO$_2$—C$_6$H$_4$—Cl | 52.87 <br> (53.24 <br> (1.0 mole H$_2$O) | 6.07 <br> 6.20 | 7.78 <br> 8.01) |
| 217 | H$_2$N(CH$_2$)$_4$CHCONH— <br> \| <br> NHCH$_2$C$_6$H$_5$ <br> (1) | 61.04 <br> (62.52 <br> (1.0 mole H$_2$O) | 7.14 <br> 7.54 | 8.57 <br> 9.11) |
| 218 | H$_2$N(CH$_2$)$_4$CHCONH— <br> \| <br> CH$_3$ <br> (R) | 52.37 <br> (54.44 | 7.10 <br> 1.01 | 6.81 <br> 7.18) |
| 219 | H$_2$N(CH$_2$)$_4$CHCONH— <br> \| <br> CH$_2$C$_6$H$_5$ <br> (R) | 64.00 <br> (66.06 | 7.40 <br> 7.45 | 7.00 <br> 7.22) |
| 220 | H$_2$N(CH$_2$)$_4$CHCONH— <br> \| <br> CH$_2$OH <br> (R) | 57.83 <br> (55.84 <br> 2.0 mole H$_2$O, 0.5 mole EtOH) | 7.90', 76 <br> 7.98 | 7.22 <br> 7.23) |
| 221 | H$_2$N(CH$_2$)$_5$CONH— | 56.69 <br> (61.08 | 7.82 <br> 7.59 | 7.04 <br> 8.55) |
| 222 | CH$_3$S(CH$_2$)CHCONH— <br> \| <br> NHCH$_2$C$_6$H$_5$ | 58.75 <br> (58.52 | 6.99 <br> 6.65 | 6.21 <br> 6.60) |
| 223 | H$_2$N(CH$_2$)$_4$CHCONH— <br> \| <br> (CH$_2$)$_3$C$_6$H$_5$ <br> (R) | 64.09 <br> (66.97 | 7.39 <br> 7.77 | 6.64 <br> 6.89) |
| 224 | NH—CH$_2$CONH— (pyrrolidine) | 53.82 <br> (54.06 <br> (0.2 mole CH$_2$Cl$_2$, H$_2$O, HCl) | 6.56 <br> 6.73 | 6.53 <br> 7.50) |
| 225 | H$_2$N(CH$_2$)$_4$CHNCH$_3$— <br> \| <br> NHSO$_2$CH$_3$ | 52.36 <br> (54.08 <br> (0.5 mole EtOH) | 7.24 <br> 7.29 | 8.33 <br> 9.01) |
| 226 | H$_2$N(CH$_2$)$_4$CHCONCH$_3$— <br> \| <br> NH$_2$ | 57.82 <br> (59.7 <br> (0.3 mole EtOH) | 7.94 <br> 7.89 | 10.03 <br> 10.45) |
| 227 | H$_2$N(CH$_2$)$_4$NHCO— (2) | 57.72 <br> (57.63 <br> (1.25 mole H$_2$O) | 7.58 <br> 7.56 | 7.20 <br> 8.40) |

-continued

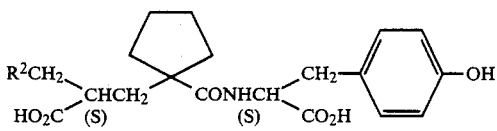

| Example No | R² | Analysis % (Theoretical in brackets) C | H | N |
|---|---|---|---|---|
| 228 | CH₂C₆H₅<br>\|<br>H₂N(CH₂)₄NCO—    (2) | Rf 0.46<br>(MIBK, H₂O, AcOH, 2:1:1) | | |
| 229 | CH₂OH<br>\|<br>H₂N(CH₂)₄CHNHCO—<br>(S) | Rf 0.15<br>(MIBK, H₂O, AcOH, 2:1:1) | | |
| 230 | NH₂<br>\|<br>H₂NCH₂CHCONH—<br>(S) | 48.03<br>(48.12<br>(H₂O, 0.25 mole Et₂O,<br>2HCl) | 6.74<br>6.76 | 8.72<br>9.76) |
| 231 | NH₂<br>\|<br>HOCH₂CHCONH—<br>(R) | 50.83<br>(50.92<br>(HCl, H₂O, 1 mole<br>EtOH) | 6.74<br>7.12 | 7.21<br>7.42) |
| 232 | NH₂<br>\|<br>HOCH₂CHCH₂CONH—<br>(R) | 51.97<br>(52.59<br>(HCl, 0.5 H₂O 0.5 mole<br>EtOH) | 7.13<br>6.98 | 7.35<br>7.67) |
| 233 | NH₂<br>\|<br>(CH₃)₂CHCH₂CHCONH— | 59.09<br>(58.92<br>(hydrate) | 7.54<br>6.73 | 8.27<br>8.25) |
| 234 | H₂N—[pyrrolidine]—N—COC₆H₅<br>                          CONH— (S) | 58.53<br>(58.53<br>(0.5 mole Et₂O, 0.5 H₂O, HCl) | 6.65<br>6.70 | 8.41<br>8.27) |
| 235 | NH₂<br>\|<br>CH₃(CH₂)₃CHCONH— (S) | 57.24<br>(56.86 | 7.44<br>7.25 | 7.29<br>7.95) |
| 236 | NH₂<br>\|<br>C₆H₅CH₂OCH₂CHCONH—<br>(S) | 57.58<br>(57.23<br>(0.6 H₂O, 0.5 mole dioxan) | 6.68<br>6.88 | 6.38<br>6.46) |
| 237 | CH₃   NH₂<br>\|       \|<br>C₆H₅CH₂OCH—CHCONH—<br>(R)   (S) | 55.48<br>(55.55<br>(HCl, 2.3 H₂O, 0.16 mole EtOH) | 6.74<br>7.01 | 6.22<br>6.41) |
| 238 | [imidazole]—CH₂CHCONH—<br>               \|<br>               NH₂<br>(S) | 53.72<br>(53.50<br>(1.25 H₂O, 0.25 mole Et₂O) | 6.48<br>7.08 | 11.46<br>12.00) |
| 239 | CH₃   NH₂<br>\|       \|<br>C₆H₅CH₂OCH—CHCONH—<br>(R)   (R) | 58.85<br>(59.23<br>(HCl, 0.1 Et₂O, 0.1 mole<br>PhOMe) | 6.73<br>6.57 | 6.65<br>6.89) |

-continued

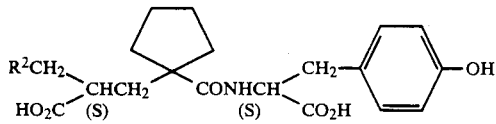

| Example No | R² | Analysis % (Theoretical in brackets) | | |
|---|---|---|---|---|
| | | C | H | N |
| 240 | N=CH-NH-C(=CH-)-CH₂CH(NHCOCH₃)CONH— (S) | 57.26 (57.23 (0.5 mole H₂O) | 6.39 6.40 | 12.20 12.36) |
| 241 | imidazol-N-CH₂CH(NHCOCH₃)CONH— (R,S) | 53.16 (53.37 (HCl, 0.5 mole H₂O) | 6.09 6.22 | 10.26 11.53) |
| 242 | HO—C₆H₄—CH(NH₂)CONH— (R) | 57.12 (57.05 (HCl) | 6.26 6.08 | 6.42 7.45) |
| 243 | C₆H₅CH₂O—CH₂CH(NH₂)CH₂CONH— (R) | 58.77 (58.58 (HCl, 0.5 mole H₂O) | 6.78 6.71 | 6.67 6.83) |
| 244 | H₂NCH₂CH(NHCOC₆H₅)CONH— (S) | 55.64 (55.35 (HCl, H₂O, 0.25 mole dioxane, 0.16 mole Et₂O, 0.12 mole CH₂Cl₂) | 6.41 6.48 | 7.98 8.39) |
| 245 | imidazol-CH₂-CH(CH₂OH)NHCO— (2) | 55.42 (55.60 (0.58 EtOH, 0.25CH₂Cl₂, 0.75 H₂O) | 6.57 6.72 | 9.14 9.40) |

(1) Example 217 was prepared by Z-deprotection using HBr in acetic acid.
(2) With the exception of Examples 227–229 and 245 the compounds are resolved S,S-isomers.

EXAMPLES 246–259

The following compounds were prepared from the appropriate t-butyl or benzyl ester/t-butoxycarbonyl or benzyloxycarbonyl protected compound by treatment with HCl and/or hydrogenation following the procedures of Examples 176 and 177 as appropriate. Moities derived from lysine and tyrosine are of (S) stereochemistry unless otherwise stated. Examples 249, 251, 252, 258 and 259 are fully resolved S,S,S isomers.

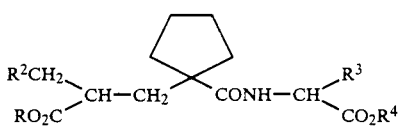

| Example No | R | R² | R³ | R⁴ | Analysis % (Theoretical in brackets) | | |
|---|---|---|---|---|---|---|---|
| | | | | | C | H | N |
| 246 | (dimethylmaleic anhydride-CH₂-) | NHSO₂CH₃<br>H₂N(CH₂)₄CHCONH— | 4-HOC₆H₄-CH₂— | H | 58.66<br>(58.13 | 7.59<br>7.54 | 5.39<br>6.16) |
| 247 | H | NHSO₂CH₃<br>H₂N(CH₂)₄CHCONH— | 4-(CH₃CH₂OCO₂)C₆H₄-CH₂— | —CH₂CH₃ | 51.60<br>(51.64<br>(HCl) | 7.12<br>6.88 | 7.37<br>7.77) |
| 248 | H | NHSO₂CH₃<br>H₂N(CH₂)₄CHCONH— | 4-(cyclohexyl-OCO₂)C₆H₄-CH₂— | cyclohexyl | 55.85<br>(55.86<br>(HCl, 0.5 mole H₂O) | 7.37<br>7.45 | 6.48<br>6.68) |
| 249 | H | NHCH₂CH₃<br>H₂N(CH₂)₄CHCONH— | 4-HOC₆H₄-CH₂— | H | 58.94<br>(60.65 | 8.10<br>7.92 | 10.14<br>10.48) |
| 250 | CH₃CH₂— | NH₂<br>ZNH(CH₂)₄CHCONH— | 4-HOC₆H₄-CH₂— | CH₃CH₂ | 59.77<br>(59.87<br>(HCl, 0.5 mole H₂O) | 7.67<br>7.33 | 7.67<br>7.55) |
| 251 | H | NHCOCH₃<br>H₂N(CH₂)₄CHCONH— | 3-(CH₃SO₂NH)C₆H₄-CH₂— | H | 53.07<br>(52.98<br>(0.5 mole H₂O) | 7.05<br>6.98 | 11.62<br>11.03) |
| 252 | (CH₃)₃C— | NH₂<br>BOCNH(CH₂)₄CH—CONH— | 4-(CH₃)₃CO-C₆H₄-CH₂— | —C(CH₃)₃ | 63.85<br>(65.08 | 9.03<br>9.10 | 7.10<br>7.23) |

-continued

| Example No | R | R² | R³ | R⁴ | Analysis % (Theoretical in brackets) C | H | N |
|---|---|---|---|---|---|---|---|
| 253 | CH₃CH₂— | NHSO₂CH₃ \| H₂N(CH₂)₄CHCONH— | —CH₂—C₆H₄—OH | —CH₂CH₃ | 52.69 (52.54 (2.5 mole H₂O) | 7.60 7.78 | 7.68 8.16 |
| 254 | CH₃CH₂— | NHSO₂CH₃ \| NH₂(CH₂)₄CHCONH— | —CH₂—C₆H₄—OH | H | 53.06 (53.31 | 7.41 7.35 (H₂O) | 8.50 8.88 |
| 255 | C₆H₅(CH₂)₃— | NHSO₂CH₃ \| H₂N(CH₂)₄CHCONH— | —CH₂—C₆H₄—OH | H | 58.93 (59.81 | 7.31 7.17 | 7.21 7.97 |
| 256 | CH₃CH₂ | NHSO₂CH₃ \| H₂N(CH₂)₄CHCONH— | —CH₂—C₆H₄—OH | —CH₃CH₂ | 52.69 (52.54 (2.5 mole H₂O) | 7.60 7.78 | 7.68 8.16 |
| 257 | (CH₃)₃Si(CH₂)₂ | NH₂ \| BOCNH(CH₂)₄CHCONH— | —CH₂—C₆H₄—OC(CH₃)₃ | —C(CH₃)₃ | 62.90 (63.05 | 9.55 9.11 | 6.49 6.84 |
| 258 | (CH₃)₃Si(CH₂)₂ | NH₂ \| BOCNH(CH₂)₄CHCONH— | —CH₂—C₆H₄—OC(CH₃)₃ | —C(CH₃)₃ | 62.76 (63.05 | 9.13 9.11 | 6.53 6.84 |
| 259 | (CH₃)₃Si(CH₂)₂ | NH₂ \| BOCNH(CH₂)₄CHCONH— | —CH₂—C₆H₄—NHSO₂CH₃ | —C(CH₃)₃ | 56.56 (56.58 0.5 H₂O | 8.31 8.31 | 8.16 8.24 |

EXAMPLES 260-263

The following compounds were prepared by deprotection of the corresponding N-butyloxycarbonyl or N-benzyloxycarbonyl derivative following the procedure of Example 176 or 177 starting with the appropriate S,S,S isomer.

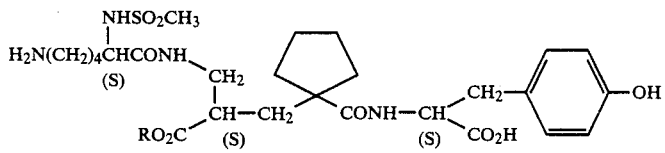

| Example No | R | Analysis (Theoretical in brackets) | | |
|---|---|---|---|---|
| | | C | H | N |
| 260 | $(CH_3)_3CCO_2CH_2-$ | 52.25 (52.27 | 7.32 6.99 (HCl) | 7.37 7.62) |
| 261 | cyclohexyl-$CO_2CH(CH_3)-$ | 55.01 (54.21 | 7.60 7.15 (HCl) | 7.01 7.22) |
| 262 | $CH_3CH_2CO_2C-$ with $CH(CH_3)_2$ | 52.61 (52.89 | 7.07 7.13 (HCl) | 7.43 7.47) |
| 263 | indanyl-methyl | 58.07 (58.47 | 7.27 7.01 ($H_2O$) | 7.70 7.79) |

EXAMPLE 264

N-{1-[3(N²-Acetyl-(S)-lyslyamino)-2-carboxypropyl]-1-cyclopentanecarboyl}-3-methanesulphonsmido-(R,S)-phenylalanine A solution of N-{1-[3-N²-acetyl-(S)-lysylamino-2-carboxypropyl]-1-cyclopentanecarbonyl]}-3-methanesulphonamido-(R,S)-phenylalanine ethyl ester (from Example 19, 0.21 g) in ethanol (10 ml) was treated with sodium hydroxide solution (5 ml N) and the solution stirred at room temperature for 3½ hours. The reaction mixture was poured onto a column of a strongly acidic ion-exchange resin, which was washed to neutrality and the product subsequently eluted with aqueous pyridine (3%). Evaporation of the product containing fractions gave the title dicarboxylic acid glass (0.092 g, 46%), m.p. 160°-164° C. Found: C,51.32; H,6.86; N, 10.75; $C_{28}$; $H_{43}N_5O_9S$ (1.5 $H_2O$) requires C,51.52; H,7.10; N,10.73%.

EXAMPLES 265-273

The following products were prepared following the procedure of Example 264 starting with the appropriate ethyl ester.

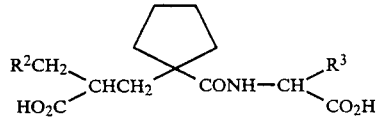

Examples 267 and 273 are resolved compounds having S,S,S, stereochemistry.

| Example No. | $R^2$ | $R^3$ | Analysis % (Theoretical in Brackets) | | |
|---|---|---|---|---|---|
| | | | C | H | N |
| 265 | $H_2N(CH_2)_4CHCONH-$ with $NH_2$ (S) | $-CH_2-$phenyl-$NHSO_2CH_3$ (R,S) | 52.79 (52.69 (0.5 mole $H_2O$) | 7.21 7.14 | 11.86 11.82 |
| 266 | $H_2N(CH_2)_4CHCONH-$ with $NHSO_2CH_3$ (S) | $-CH_2-$phenyl-$NHSO_2CH_3$ (R,S) | 47.95 (47.90 (hydrate) | 6.60 6.67 | 10.26 10.30 |
| 267 | $H_2N(CH_2)_4CHCONH-$ with $NHCOCH_3$ (S) | $-CH_2-$phenyl-$NHSO_2CH_3$ (S) | 53.07 (52.98 (0.5 mole $H_2O$) | 7.05 6.98 | 11.62 11.03 |

-continued

| Example No. | R² | R³ | Analysis % (Theoretical in Brackets) | | |
|---|---|---|---|---|---|
| | | | C | H | N |
| 268 | H₂N(CH₂)₄CHCONH— with NH₂ substituent (S) | —CH₂—C₆H₄—OCH₃ (S) | 56.69 (57.02 (1.5 mole H₂O) | 7.80 7.64 | 10.01 10.23 |
| 269 | H₂N(CH₂)₄CHCONH— with NHSO₂CH₃ substituent (S) | —CH₂—C₆H₄—OCH₃ (S) | 51.88 (51.82 (1.5 mole H₂O) | 7.14 7.24 | 7.20 8.95 |
| 270 | H₂N(CH₂)₄CHCONH— with OH substituent (S) | —CH₂—C₆H₄—OCH₃ (S) | 58.95 (58.85 (0.5 mole H₂O) | 7.75 7.60 | 7.92 7.92 |
| 271 | H₂N(CH₂)₄CHCONH— with NHCO-furyl substituent (S) | —CH₂—C₆H₄—OCH₃ (S) | 58.54 (58.84 (1.0 mole H₂O) | 7.04 7.01 | 8.76 8.85 |
| 272 | H₂N(CH₂)₄CHCONH— with NHCO-cyclobutyl substituent (S) | —CH₂—C₆H₄—OCH₃ (S) | 59.82 (59.98 (1.0 mole H₂O) | 7.67 7.79 | 9.23 9.02 |
| 273 | H₂N(CH₂)₄CHCONH— with NHCOCH₃ substituent (S) | —CH₂—C₆H₄—OCH₃ (S) | 57.00 (57.02 (1.5 mole H₂O) | 7.75 7.44 | 9.63 9.50 |

EXAMPLE 274

N-{[3-(N²-Methanesulphonyl-(S)-lysylamino)-2-(S)-carboxypropyl]-1-cyclopentanecarboyl}-3-methanesulphonamido-(S)-phenylalanine The title compound was prepared from Example 259 in the following manner: The N²-methanesulphonyl group was introduced using the procedure of Example 157 to yield the N²-methanesulphonyl derivative as an oil. Found: C,52.09; H,7.75; N,7.32, C₄₁H₇₁N₅O₁₂S₂Si (1.5 H₂) requires C,52.09; H,7.89; N,7.41%. The trimethylsilyethyl protecting group was removed using the procedure of Example 161 to yield the monoacid as a white foam.

Found: C,51.81; H,7.30; N,7.95. C₃₆H₅₉N₅O₁₂S₂ (H₂) requires C,51.72; H,7.35; N,8.37%. And finally the title diacid was prepared from the monoacid by treatment with HCl using the procedure of Example 176 and was obtained as a white powder. Found: C,45.65; H,6.70; N,8.59. C₂₇H₄₃N₅O₁₀S₂ (1 HCl, 0.75 ethyl acetate, 1.5 H₂O) requires C,45.53; H,6.75; N,8.85%.

EXAMPLE 275

N-{1-[3-(S)-Lysylamino-2-(S)-carboxypropyl]-1-cyclopentane-N-}-3-methanesulfphonamide-(S)-phenylalanine The title compound was prepared from Example 150 in the following manner: The trimethylsilylethyl protecting group was removed using the procedure of Example 161 to yield the monoacid as a white foam. Found: C,57.66; H,7.17; N,7.62. C₄₃H₆₃N₅O₁₂S(H₂) requires C,57.89; H,7.34; N,7.85%. Further deprotection using the procedure of Example 176 gave the diacid as a white foam. Found: C,51.02; H,6.46; N,8.33. C₃₄H₄₇N₅O₁₀S (HCl, 2.5 H₂) requires C,51.09; H,6.68; N,8.76%. The benzyloxycarbonyl group was then removed using the procedure of Example 177 to give the title compound as a white powder. Rƒ0.17 (methyl isobutylketone, water, acetic acid, 2:1:1).

EXAMPLE 276

N-{1-[3(N²-Methanesulphonyl-(R,S)-(1-imidazolyl)alanylamino)-2(S)-carboxypropyl]-1-cyclopentanecarbonyl}-(S)-tyrosine N²-Methanesulphonyl-(R,S)-(1-imidazolyl)alanine was coupled to N-[1-(3-aminopropyl-2(S)-t-butyloxycarbonyl)-1-cyclopentanecarbonyl]-O-t-butyl-(S)-tyrosine t:butyl ester (Example 56) using the procedure of Example 81 to give the product as a white foam. Found: C,59.46; H,7.90; N,9.04. $C_{38}H_{59}N_5O_9S$ requires C,59.89; H,7.80; N,9.19%. This material was deprotected by treatment with the HCl using the procedure of Example 176 to give the title compound as a white powder. $R_f$ 0.30 (methyl isobutylketone, water, acetic acid 2:1:1).

EXAMPLE 277

N-{1-[3-(N²Methanesulfphonyl-N2-methyl-(S)-lysylamino)-2-carboxypropyl]-1-cyclopentanecarbonyl}-(S)-tyrosine N⁶-Benzyloxycarbonyl-N²-methanesulphonyl-N²methyl-lysine was N6-Benzyloxycarbonyl-N2-methanesulphonyl-N coupled to N-[1-(3-aminopropyl-2(S)-t-butyloxycarbonyl)-1-cyclopentanecarbonyl]-O-t-butyl-(S)-tyrosine t-butyl ester (Example 56) using the procedure of Example 81 to give the product as a white foam. Found: C,62.40; H,8.17; N,6.30. $C_{47}H_{72}N_4O_{11}S$ requires foam. C,62.64; H,8.05; N,6.22%.

Deprotection of this material following the procedures of Examples 176 and 177 gave the title compound. Found C,50.26; H,7.17; N,8.60. $C_{27}H_{42}Nhd 4O_9S$ (2.5 $H_2$) requires C,50.37; H,7.36; N,8.70%.

EXAMPLE 278

N-{1-0[3-(N²-Methanesulphonyl-(S)-lysylamino)-2-(S)-carboxypropyl]-(N1-cyclopentanecarbonyl}-S-tyrosinamide The title compound was prepared from Example 164 by coupling with ammonia using the procedure of Example 171 to give the primary amide as a white foam. Deprotection of this material with HCl using the procedure of Example 176 gave the title compound as a white powder. Found: C,53.02; H,7.38; N,11.26. $C_{26}H_{41}N_5O_8S$ (0.45 $H_2O$) requires C,52.76; H,7.14; N,11.83%.

EXAMPLE 279

N-{1-[3-(N²-Methanesulphonyl-(S)-lysylamino)-N-2-(1-(R,S)-isobutyryloxyethoxy)carbonylpropyl-1-cyclopentantecarboyl}-(S)-tyrosine cyclopentantecar The title compound was prepared in the following manner: Alkylation of the product of Example 161 with 1-(R,S)-isobutyryloxyethyl chloride using the procedure of Example 166 gave the protected ester as a white foam. Found: C,57.36; H,7.91; N,5.74. $C_{45}H_{74}N_4O_{13}S$ (05 $CH_2Cl_2$) requires C,57.30; H,7.93; N,5.88%. Deprotection of this product with HCl using the procedure of Example 176 gave the title ester as a white powder. Found: 51.32; H,7.25; N,6.86. $C_{32}H_{50}N_4O_{11}S$ (HCl, $H_2$) requires C,51.02; H,7.09; N,7.43%.

EXAMPLE 280

N-{1-[3-(N2-Methanesulphonyl-(S)-lysylamino)2-(1-(R,S)benzoyloxyethoxy)carbonylpropyl]-1-cyclopentanecarbonyl}-(S)-tyrosine The title compound was prepared by alkylation of the product of Example 161 with 1-(R,S)-benzyloxyethyl chloride using the procedure of Example 166 to give the protected ester derivative. Deprotection of this material with HCl using the procedure Example gave the title ester as a white powder. Found: C,54.82; H,6.57; N,7.01. $C_{35}H_{47}N_4O_{11}S$ (HCl) requires C,54.72; H,6.30; N,7.29%.

What is claimed is:

1. A compound having the formula:

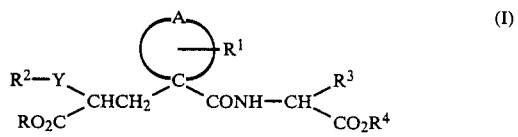

(I)

and pharmaceutically acceptable salts thereof and bioprecursors therefor wherein:

A completes a 5 or 6 membered carbocyclic ring which may be saturated or monounsaturated;

$R^1$ is H or $(C_1–C_4)$alkyl;

R and $R^4$ are each independently H, $(C_1–C_6)$alkyl $(C_3–C_7)$cycloalyl, benzyl, or an alternative biolabile ester-forming group;

Y is either a direct bond or an alkylene group of from 1 to 6 carbon atoms which may be straight or branched chain;

$R^2$ is H, aryl, heterocyclyl, $R^6CONR^5$—, $R^7NR^5CO$—, $R^7NR^5SO_2$— or $R^8SO_2NR^5$—, with the proviso that Y is not a direct bond when $R^2$ is H, aryl or heterocyclyl;

wherein $R^5$ is H, $(C_1–C_6)$alkyl or aryl $(C_1–C_6($alkyl;

$R^6$ aryl, heterocyclyl, or a group of the formula:

wherein $R^9$ is H, OH, $(C_1–C_6)$alkoxy, $(C_1–C_6)$ alkyl, hydroxy$(C_1–C_6)$alkyl, hydroxy $(C_1–C_6)$alkyl, aryl, aryl$(C_2–C_6)$ heterocyclyl, heterocyclyl $(C_1–C_6)$alkyl, $R^{12}CONH$—, $R^{12}SO_2NH$— or $(R^{13})_2N$—;

$R^{10}$ and $R^{11}$ are each independently H or )alkyl; or $R^{10}$ is H and $R^{11}$ is amino )$(C_1–C_6)$alkyl, imidazolylmethyl, aryl, aryl$(C_1–C_6)$alkyl, hydroxy $C_1–C_6)$ or methylthio )alkyl; or the two groups $R_{10}$ and $R^{11}$ are joined together to form, with the carbon atom to which they are attached, a 3 to 6 membered carbocyclic ring or a ring which may optionally be substituted by amino, $(C_2–C_4)$ alkanoyl or aroyl; or a pyrrolidine or piperidien ring which is substiuted by amino, $(C_2–C_4)$ alkanoyl or aroyl; amino, $R^{12}$ is $(C_1–C_6)$alkyl, $(C_3–C_7)$cycloalkyl, aryl, aryl $(C_1–C_6)$alkyl, heterocyclyl or heterocyclyl$(C_1–C_6)$alkyl;

$R^{13}$ is H, $(C_1–C_6)$alkyl, aryl or the two groups $R^{13}$ are taken together to form, with the nitrogen to which they are attached, a pyrrolidinyl, piperidino, morpholino, piperazinyl or N—(C₁-C₄)alkyl-piperazinyl group;

R⁷ is (C₁-c₆)alkyl, aryl, aryl(C₁-C₆)alkyl, heterocyclyl, heterocyclyl(C₁-C₆)alkyl or a group of the formula:

wherein R¹⁰ and R¹¹ are as previously defined and R¹⁴ is (R¹³)₂NCO—, R¹²OCH₂or R¹⁵OCO, wherein R¹² an dR¹³ are as previously defined and R¹⁵ is (C₁-C₆)alkyl, (C₃-C₇)cycloalkyl or aryl(-C₁-C₆)alkyl; and R⁸ is )alkyl, aryl, aryl(C₁-C₆)alkyl, heterocyclyl or heterocyclyl(C₁-C₆)alkyl;

R³ is a group of the formula:

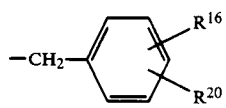

wherein R¹⁶ is H, halo 4—OH, 4-(C₁C₆alkoxy), 4-(C₃—C₇)cycloalkoxy),4-alkenyloxy), 4-[(C₁-C₆alkoxy)carbonyloxy], 4-[(C₃-C₇cycloalkoxy)carbonyloxy], or 3-(C₁-C₄ alkyl)SO₂NH—; and is H alkoxy, (C₂-C₆)alkanoyl or halo; or R³ is a group of the formula:

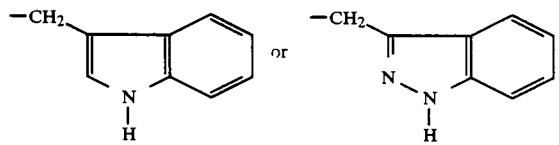

wherein said groups may optionally be substituted in the fused benzene ring by (C₁-C₄)alkyl, (C₁-C₄) alkoxy, OH, halo or CF₃.

2. A compound as claimed in claim 1 wherein A is (CH₂)₄ and R¹ is H having the formula:

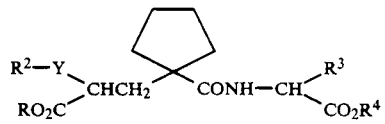

(II)

3. A compound as claimed in claim 1 or claim 2 wherein one of R and R⁴ is a biolabile ester-forming group.

4. A compound as claimed in claim 3 wherein said biolabile ester-forming group is selected from ethyl, indanyl, isopropyy, n-butyl, sec-butyl, t-butyl, cyclohexyl, benzyl, phenethyl, phenpropyl, acetonyl, glyceryl, pivaloxymethyl, 4(4-methyl-1,3-dioxolene-onyl)-methyl, cyclohexyloxycarbonyloxyethyl, butyloxycarbonyloxyethyl, isobutyloxycarbonylethyl and ethoxycarbonyloxyethyl.

5. A compound as claimed in claim 4 wherein said biolabile ester group is pivaloyloxymethyl.

6. A compound as claimed in any one of claim 2 wherein R³ is 4-hydroxybenzyl, 4-methoxybenzyl, or 4-methanesulphonamidobenzyl, and the carbon atom to which it is attached is of (S) stereochemistry.

7. A compound as claimed in any one of claim 6 wherein Y is CH₂ or a direct bond.

8. A compound as claimed in claim 7 wherein R² is a group of the formula R⁶CONR⁵.

9. A compound as claimed in claim 8 wherein R⁶ is of formula R⁹R¹⁰R¹¹C— wherein R⁹ is (R¹³)₂, N—, R¹²SO₂NH— or R¹²CONH wherein R¹² and R¹³ are as previously defined, is amino-(C₁-C₆)alkyl and R¹¹ is H.

10. A compound as claimed in claim 9 wherein R⁶CO is (S)-lysyl or N² substituted-(S)-lysyl of formula R⁹R¹⁰R¹¹CO— wherien R⁹ is NH₂, R¹²CONH or R¹²SO₂NH and R¹² is as previously defined, R¹⁰ is 4-aminobutyl and R¹¹ is H.

11. A compound as claimed in claim 10 wherein R⁶CO is (S)-lysyl, N²-methanesulphonyl-(S)-lysyl, N²-phenylsulphonyl-(S)-lysyl or N²-acetyl-(S)-lysyl.

12. A compound as claimed in claim 1 selected from: N-[1-(2(S)-carboxy-3-(S)-lysylaminopropyl)-1-cyclopentane-carbonyl]-(S)tyrosine, N-{1-[2(S)-carboxy-3-(N²-methane-sulphonyl-(S)-lysylamion)propyl]-1-cyclopentanecarbonyl}-(S)-tyrosine, N-{1-[2(S),-carboxy-3-(N²-2-furoyl-(S)-lysylamino)-propyl}-1-cyclopentanecarbonyl}-(S)-tyrosone, N-{1-[2(S)-carboxy-3(N²-acetyl-(S)-lysylamino)propyl]-1cyclopentane-carbonyl}-(S)-4-methyoxyphenylalamine, N-[1-(2-carboxyl-3-(S)-lysylaminopropyl-1-cyclopentanecarbonyl]-3-methanesulphonamido-phenylalanine, N-{1-[2-carboxyl-3-(N²-methanesulphonyl-(S)-lysylamino)-propyl]-1-cyclopentanecarbonyl}-3methanesulphonamidophenylalanine, N-{1-[2(S)-carboxyl-3-(N²-acetyl-(S)-lysylamio)-propyl]-1cycloentanecarboyl}-(S)-3-methanesulphonamidophenyl-alanine, and N-{1-[2(S)-carboxyl-3-(N²-phenylsulphonyl-(S)-lysylamino)-propyl]-1cyclopentanecarbonyl}-(S)-tyrosine, and pharmaceutically acceptable salts biolabile ester derivatives thereof.

13. A pharmaceutical composition comprising a compound of the formula (I) as claimed in claim 1 or a pharmaceutically acceptable salt thereof or bioprecursor therefor, together with a pharmaceutically acceptable diluent or carrier.

14. A method of controlling chronic hypertension or chronic hypertension complications which comprises administering to a mammal suffering from chronic hypertension a chronic hypertension controlling amount of a compound of claim 1.

* * * * *